United States Patent
Bianchi

(10) Patent No.: US 11,304,858 B2
(45) Date of Patent: *Apr. 19, 2022

(54) ABSORBENT ARTICLES WITH DIFFERENT TYPES OF CHANNELS

(71) Applicant: The Procter & Gamble Company, Cincinnati, OH (US)

(72) Inventor: Ernesto Gabriel Bianchi, Oberursel (DE)

(73) Assignee: The Procter & Gamble Company, Cincinnati, OH (US)

( * ) Notice: Subject to any disclaimer, the term of this patent is extended or adjusted under 35 U.S.C. 154(b) by 514 days.

This patent is subject to a terminal disclaimer.

(21) Appl. No.: 16/163,646

(22) Filed: Oct. 18, 2018

(65) Prior Publication Data

US 2019/0117478 A1    Apr. 25, 2019

(30) Foreign Application Priority Data

Oct. 23, 2017 (EP) ..................................... 17197839

(51) Int. Cl.
*A61F 13/538* (2006.01)
*A61F 13/42* (2006.01)
(Continued)

(52) U.S. Cl.
CPC ...... *A61F 13/538* (2013.01); *A61F 13/15634* (2013.01); *A61F 13/42* (2013.01);
(Continued)

(58) Field of Classification Search
CPC .............. A61F 13/15634; A61F 13/42; A61F 13/4704; A61F 13/49001; A61F 13/49058;
(Continued)

(56) References Cited

U.S. PATENT DOCUMENTS 3,848,594 A    11/1974    Buell
3,860,003 A    1/1975    Buell
(Continued)

FOREIGN PATENT DOCUMENTS

CN    202069776 U    12/2011
EP    149880 A2    7/1985
(Continued)

OTHER PUBLICATIONS

All Office Actions; U.S. Appl. No. 16/163,628.
(Continued)

*Primary Examiner* — Michele M Kidwell
(74) *Attorney, Agent, or Firm* — Sarah M. DeCristofaro

(57) ABSTRACT

An absorbent article has a front side, a back side, a longitudinal axis, a liquid permeable topsheet, a liquid impermeable backsheet and an absorbent core between the topsheet and the backsheet. The absorbent core includes a first type of channels, wherein the top side and the bottom side of the core wrap are bonded to another, and a second type of channels, wherein the top side and the bottom side of the core wrap are not bonded or are less bonded to one another in this second type of channels than in the first type of channels. The absorbent material may also include cellulose and superabsorbent particles.

20 Claims, 11 Drawing Sheets

(51) Int. Cl.
*A61F 13/539* (2006.01)
*A61F 13/47* (2006.01)
*A61F 13/551* (2006.01)
*A61F 13/15* (2006.01)
*A61F 13/49* (2006.01)
*A61F 13/532* (2006.01)
*A61F 13/51* (2006.01)
*A61F 13/496* (2006.01)
*A61F 13/494* (2006.01)
*A61F 13/511* (2006.01)
*A61F 13/53* (2006.01)
*A61F 13/534* (2006.01)
*A61F 13/512* (2006.01)

(52) U.S. Cl.
CPC .... *A61F 13/4704* (2013.01); *A61F 13/49001* (2013.01); *A61F 13/532* (2013.01); *A61F 13/539* (2013.01); *A61F 13/55105* (2013.01); *A61F 13/494* (2013.01); *A61F 13/496* (2013.01); *A61F 13/49058* (2013.01); *A61F 13/512* (2013.01); *A61F 2013/4708* (2013.01); *A61F 2013/5113* (2013.01); *A61F 2013/51019* (2013.01); *A61F 2013/5307* (2013.01); *A61F 2013/5349* (2013.01); *A61F 2013/5395* (2013.01)

(58) Field of Classification Search
CPC .... A61F 13/494; A61F 13/496; A61F 13/512; A61F 13/532; A61F 13/538; A61F 13/539; A61F 13/55105; A61F 2013/4708; A61F 2013/51019; A61F 2013/5113; A61F 2013/5307; A61F 2013/5349; A61F 2013/5395
See application file for complete search history.

(56) References Cited

U.S. PATENT DOCUMENTS

| | | |
|---|---|---|
| 3,929,135 A | 12/1975 | Thompson |
| 4,324,246 A | 4/1982 | Mullane et al. |
| 4,342,314 A | 8/1982 | Radel et al. |
| 4,463,045 A | 7/1984 | Ahr |
| 4,515,595 A | 5/1985 | Kievit et al. |
| 4,609,518 A | 9/1986 | Curro et al. |
| 4,629,643 A | 12/1986 | Curro et al. |
| 4,662,875 A | 5/1987 | Hirotsu et al. |
| 4,695,278 A | 9/1987 | Lawson |
| 4,699,622 A | 10/1987 | Toussant et al. |
| 4,710,189 A | 12/1987 | Lash |
| 4,795,454 A | 1/1989 | Dragoo |
| 4,808,178 A | 2/1989 | Aziz et al. |
| 4,846,815 A | 7/1989 | Scripps |
| 4,894,060 A | 1/1990 | Nestegard |
| 4,909,803 A | 3/1990 | Aziz et al. |
| 4,946,527 A | 8/1990 | Battrell |
| 4,963,140 A | 10/1990 | Robertson et al. |
| 5,006,394 A | 4/1991 | Baird |
| 5,151,092 A | 2/1992 | Buell et al. |
| 5,137,537 A | 8/1992 | Herron et al. |
| 5,221,274 A | 6/1993 | Buell et al. |
| 5,242,436 A | 9/1993 | Weil et al. |
| 5,433,715 A | 7/1995 | Tanzer et al. |
| 5,499,978 A | 3/1996 | Buell et al. |
| 5,549,791 A | 8/1996 | Herron et al. |
| 5,591,152 A | 1/1997 | Buell et al. |
| 5,607,760 A | 3/1997 | Roe |
| 5,609,587 A | 3/1997 | Roe |
| 5,643,588 A | 7/1997 | Roe et al. |
| 5,837,352 A | 11/1998 | English et al. |
| 5,843,056 A | 12/1998 | Good et al. |
| 5,968,025 A | 10/1999 | Roe et al. |
| 6,075,179 A | 6/2000 | McCormack et al. |
| 6,336,922 B1 | 1/2002 | VanGompel et al. |
| 6,432,098 B1 | 8/2002 | Kline et al. |
| 6,632,504 B1 | 10/2003 | Gillespie et al. |
| 6,645,569 B2 | 11/2003 | Cramer et al. |
| 6,716,441 B1 | 4/2004 | Osborne et al. |
| 6,863,933 B2 | 3/2005 | Cramer et al. |
| 7,112,621 B2 | 9/2006 | Rohrbaugh et al. |
| 7,744,576 B2 | 6/2010 | Busam et al. |
| 7,786,341 B2 | 8/2010 | Schneider |
| 9,295,593 B2 | 3/2016 | Van Malderen |
| 9,987,176 B2* | 6/2018 | Roe ............... A61F 13/533 |
| 10,485,713 B2 | 11/2019 | Schonbeck |
| 2003/0105190 A1 | 6/2003 | Diehl et al. |
| 2003/0148684 A1 | 8/2003 | Cramer et al. |
| 2004/0023583 A1 | 2/2004 | Venturino et al. |
| 2004/0034327 A1 | 2/2004 | Kuen et al. |
| 2005/0008839 A1 | 1/2005 | Cramer et al. |
| 2007/0118087 A1 | 5/2007 | Flohr et al. |
| 2008/0312617 A1 | 12/2008 | Hundorf et al. |
| 2008/0312622 A1 | 12/2008 | Hundorf et al. |
| 2008/0312624 A1 | 12/2008 | Hundorf et al. |
| 2011/0073513 A1* | 3/2011 | Weisman ........ A61F 13/15203 206/494 |
| 2011/0250413 A1 | 10/2011 | Lu et al. |
| 2011/0268932 A1 | 11/2011 | Catalan et al. |
| 2011/0319846 A1 | 12/2011 | Rinnert et al. |
| 2011/0319848 A1 | 12/2011 | McKiernan et al. |
| 2012/0312491 A1 | 12/2012 | Jackels et al. |
| 2012/0316526 A1 | 12/2012 | Rosati et al. |
| 2012/0316527 A1 | 12/2012 | Rosati et al. |
| 2012/0316528 A1* | 12/2012 | Kreuzer ............. A61F 13/536 604/366 |
| 2012/0330262 A1 | 12/2012 | Lawson et al. |
| 2012/0330263 A1 | 12/2012 | Lawson et al. |
| 2013/0165882 A1* | 6/2013 | Kawakami ........ A61F 13/47218 604/374 |
| 2013/0226120 A1 | 8/2013 | Van De Maele |
| 2014/0039434 A1 | 2/2014 | Xu et al. |
| 2014/0039438 A1 | 2/2014 | Ferrer et al. |
| 2014/0121621 A1 | 5/2014 | Kirby et al. |
| 2014/0121623 A1 | 5/2014 | Biggs et al. |
| 2014/0121624 A1 | 5/2014 | Kirby et al. |
| 2014/0121625 A1 | 5/2014 | Kirby et al. |
| 2014/0163501 A1 | 6/2014 | Ehrnsperger et al. |
| 2014/0163503 A1* | 6/2014 | Arizti ............... A61F 13/53747 604/366 |
| 2014/0163506 A1 | 6/2014 | Roe et al. |
| 2014/0163511 A1 | 6/2014 | Roe et al. |
| 2014/0303583 A1 | 10/2014 | Berrizbeitia et al. |
| 2014/0371701 A1 | 12/2014 | Bianchi et al. |
| 2015/0080821 A1* | 3/2015 | Peri ..................... C08J 3/245 604/366 |
| 2015/0173977 A1 | 6/2015 | Stelzig et al. |
| 2015/0223990 A1 | 8/2015 | Armstrong-Ostle et al. |
| 2015/0223991 A1 | 8/2015 | Jackels |
| 2015/0342796 A1 | 12/2015 | Bianchi et al. |
| 2016/0030256 A1 | 2/2016 | Kreuzer et al. |
| 2016/0104185 A1 | 4/2016 | Seo |
| 2016/0206482 A1* | 7/2016 | Nishikawa ............ A61F 13/533 |
| 2016/0235602 A1* | 8/2016 | Ehrnsperger ......... A61F 13/494 |
| 2016/0270986 A1 | 9/2016 | Stiehl et al. |
| 2016/0341653 A1 | 11/2016 | Molas et al. |
| 2017/0135870 A1 | 5/2017 | Kamphus |
| 2019/0117476 A1* | 4/2019 | Bianchi ............. A61F 13/538 |
| 2019/0177477 A1* | 6/2019 | Ota ..................... C08G 65/333 |
| 2020/0108168 A1* | 4/2020 | Turner ................. A61F 13/514 |

FOREIGN PATENT DOCUMENTS

| | | | | |
|---|---|---|---|---|
| EP | 3403626 | * | 11/2018 | ........... A61F 13/475 |
| WO | WO9524173 | | 9/1995 | |
| WO | WO9534329 | | 12/1995 | |
| WO | 0032147 A1 | | 6/2000 | |
| WO | WO200071067 | | 11/2000 | |
| WO | 2012170778 | | 12/2012 | |
| WO | 2014093129 A1 | | 6/2014 | |
| WO | 2015/031225 | * | 3/2015 | ........... A61F 13/494 |

(56) References Cited

FOREIGN PATENT DOCUMENTS

| WO | 2015183668 A1 | 12/2015 |
| WO | 2016191260 A1 | 12/2016 |
| WO | 2017087158 A1 | 5/2017 |

OTHER PUBLICATIONS

All Office Actions; U.S. Appl. No. 16/163,635.
PCT Search Report and Written Opinion for PCT/US2018/054791 dated Jan. 17, 2019.
Extended European Search Report and Search Opinion; Application Ser. No. 17197839.8 dated Feb. 7, 2018; 10 pages.

\* cited by examiner

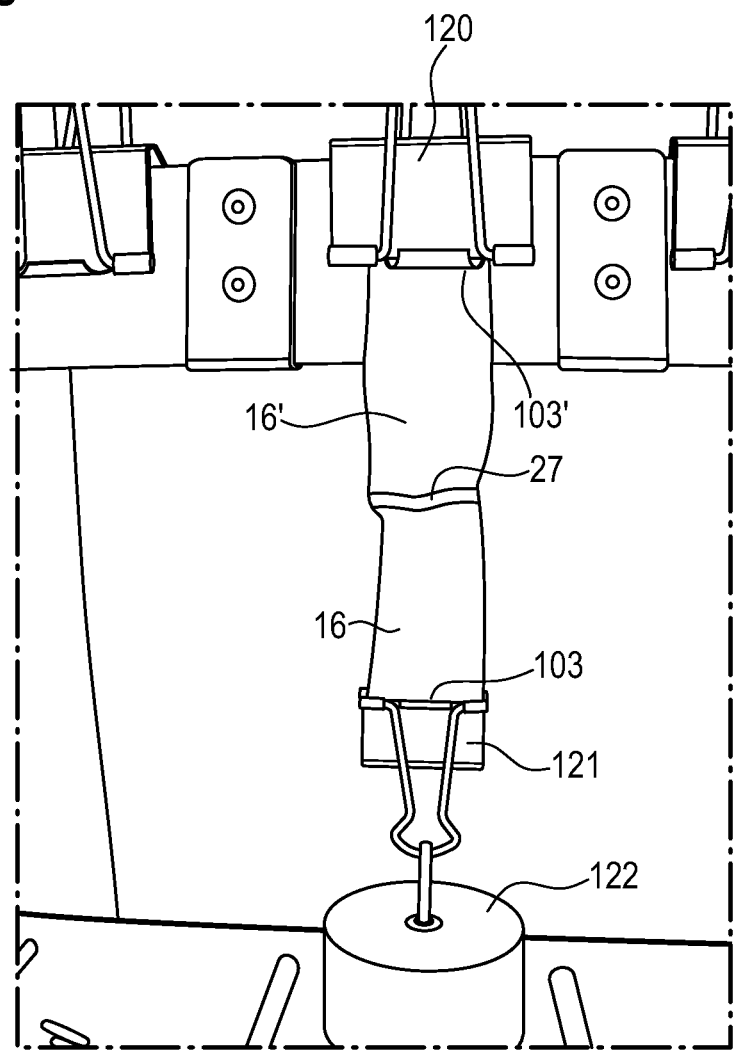

ABSORBENT ARTICLES WITH DIFFERENT TYPES OF CHANNELS

FIELD OF THE INVENTION

The invention relates to personal hygiene absorbent articles that are placed in the crotch region of a wearer to absorb body exudates, such as baby taped diapers, baby pant-like diapers, training pants, feminine pads and adult incontinence products.

BACKGROUND OF THE INVENTION

Absorbent articles for personal hygiene are designed to absorb and contain body exudates, in particular large quantity of urine. These absorbent articles comprise a topsheet on the wearer-facing side that quickly acquires the fluid and feels soft on the wearer's skin, an absorbent core for retaining the fluid, and a backsheet on the garment-facing side for protecting the wearer's clothes.

The absorbent core comprises an absorbent material that may be disposed in a core wrap. The core wrap may be typically comprised of one sheet of core wrap material folded over itself around the absorbent material or alternatively from two sheets of core wrap material forming respectively a top side and a bottom side of the core wrap, with suitable attachment along the longitudinal edges and optionally the front and back edges. The core wrap material is typically a low basis weight nonwoven. The absorbent material usually comprises superabsorbent polymers (SAP) as is known in the art. The SAP is typically distributed in the form of small particles, which may be blended with cellulose fibers in so-called airfelt cores. The SAP particles typically represent from 40% to 70% of the weight of the absorbent material, the rest being cellulose fibers. More recently, so called pulp-less or airfelt-free absorbent cores have been put on the market, wherein the absorbent material does not comprise cellulose fibers. In these airfelt-free cores, the SAP particles have been enclosed in pockets, see for example U.S. Pat. No. 5,433,715 (Tanzer et al.), WO2012/052172 (Van Malderen), or have been immobilized by a fibrous network of adhesive fibers (e.g. US2008/312617, Hundorf et al.).

Absorbent cores comprising channels for directing the fluid over a larger area of the absorbent core in a more efficient way than by diffusion have been proposed. Various channel constructions have been proposed. The channels may be macroscopic areas which are substantially free of absorbent material. Channels without any bond or immobilization, so that they quickly disappear as the absorbent material starts to swell and fills the channels, are known. Bonded channels have also been proposed in which the top side of the core wrap is bonded to the bottom side of the core wrap through the channels. This provides more permanent channels that remain in place even after the absorbent core has absorbed a substantial amount of fluid. The two sides of the core wrap may be bonded using known bonding techniques such as adhesive bonding, mechanical bonding, thermo-bonding, or ultra-sonic bonding. Examples of such bonded channels are disclosed for example in WO2012/170778A1 (Rosati et al.) and WO2014/93129 (Roe et al.). Advantages of such bonded channels are improved fit, less core sagging and better fluid distribution. These bonded channels may gradually open during use to free up more space for the swelling SAP, as for example disclosed in WO2014/200794 (Bianchi et al.). Such semi-permanent channels can be advantageous to release more free space for the absorbent material to swell as the absorbent core is loaded while keeping the benefits of permanent channels. The rate and pattern at which the bonded channels of the prior art open is however difficult to control and depend on many factors such as the pressure applied on the article, the distribution of SAP in the core, etc.

While it was found relatively easy to make channel bonds, it can be more difficult to provide semi-permanent bonds that open gradually in controlled manner. This is especially true when the absorbent material comprises cellulose fibers, because these absorbent core structures typically have a relatively high caliper and volume already in dry state, thus being more susceptible to experience swelling constraint once they start to swell. The present invention addresses the issue of providing improved absorbent cores having the benefits of semi-permanent channels in a more controllable manner.

SUMMARY OF THE INVENTION

The invention is in a first aspect directed to an absorbent article such as a diaper having an absorbent core with two different types of channels. The first type of channels may have relatively strong bonds between the top side and the bottom side of the core wrap. On the other hand, the second type of channels may have no bonds at all or at least significantly weaker bonds than the bonds of the first type of channels. The channels of the first type provide the benefits of channels in wet and dry state, while channels of the second type provide benefits at an early stage of usage when the diaper is dry or starts to be wet, but can quickly open to release free space for swelling. In a second aspect, the invention is directed to absorbent cores having these different types of channels, a method for making these absorbent cores, and packages comprising these absorbent articles.

Further advantageous aspects of the present invention are disclosed in the following description and claims. The channels of the first and second type may in particular be each respectively provided as a pair of channels disposed symmetrically relative to the longitudinal axis of the article. The first type of channels may be disposed at least partially within the crotch region of the article, and the second type of channels may be at least partially disposed in the front region and/or back region of the article. The first type of channels and the second type of channels may optionally be separated from each other by a separating zone comprising absorbent material. At least some of the first and/or second type of channels may optionally not reach any of the edges of the deposition area of the absorbent material, and thus be fully encompassed within the absorbent layer. The absorbent material comprises a blend of cellulose fibers and SAP particles. This and various other aspects of the invention are described in the following description and attached claims.

BRIEF DESCRIPTION OF THE DRAWINGS

FIG. 12 shows the tester with the cut sample of FIG. 11 for measuring the SPFT.

For ease of discussion, the absorbent cores and articles of the invention will be discussed with reference to these Figures and the numerals referred therein, however these are not intended to limit the scope of the claims unless specifically indicated.

DETAILED DESCRIPTION OF THE INVENTION

General Description of an Absorbent Article 20

Figure 1:
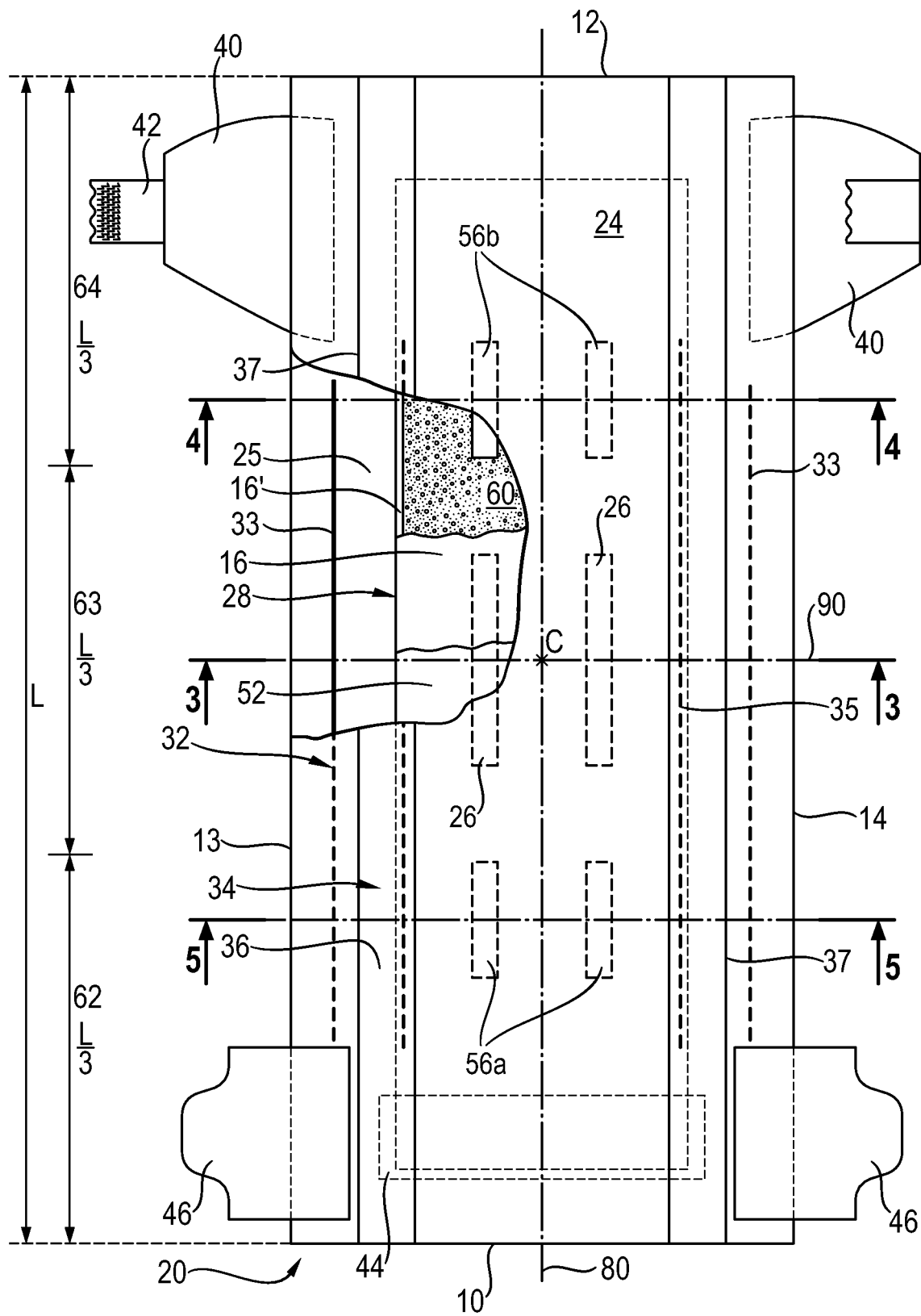
FIG. 1 is a top view of the wearer-facing side of an exemplary article of the invention in the form of a taped diaper which has been pulled flat, with some layers partially removed.
Figure 2:
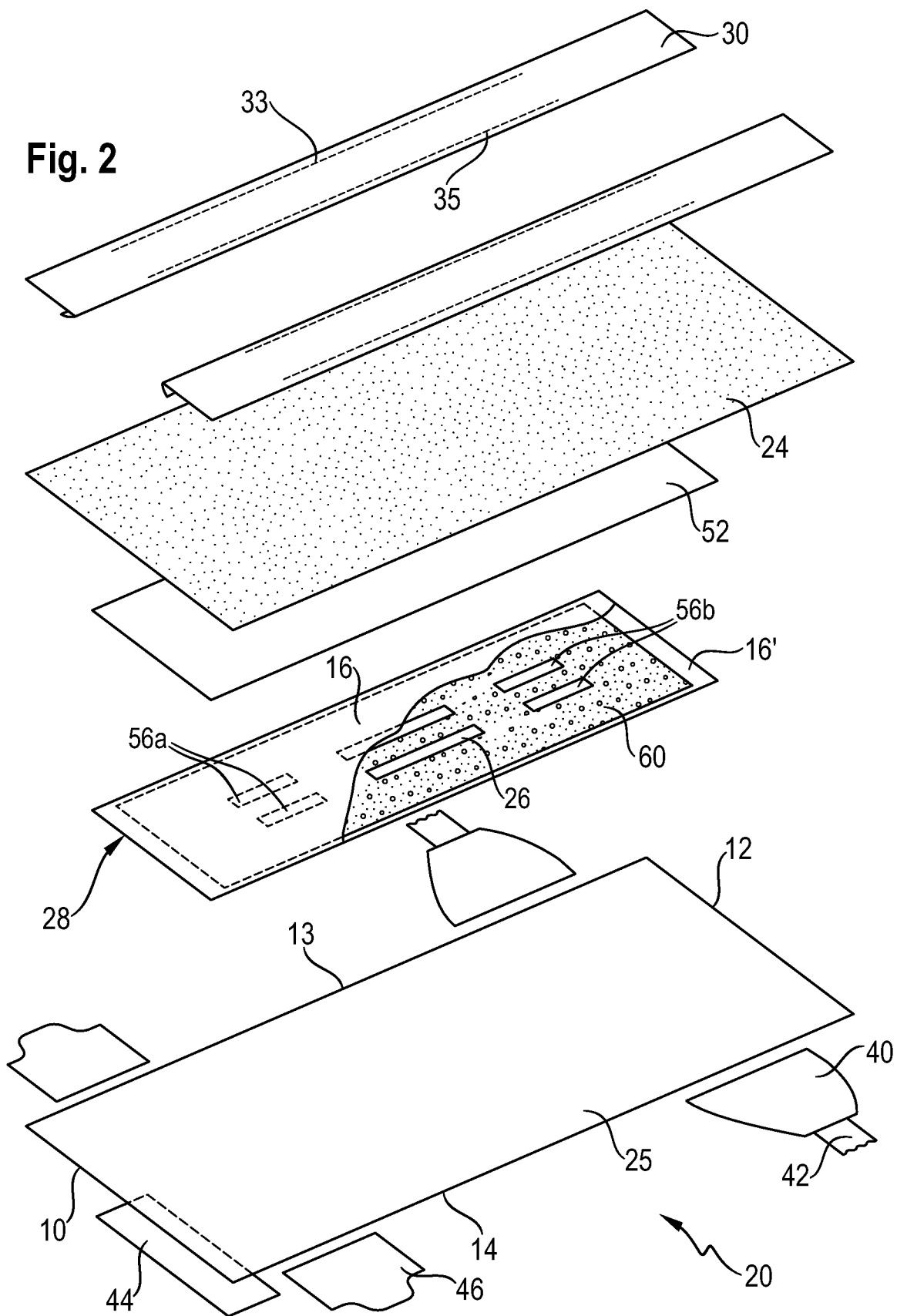
FIG. 2 shows a partial exploded view of the taped diaper of FIG. 1.
Figure 3:
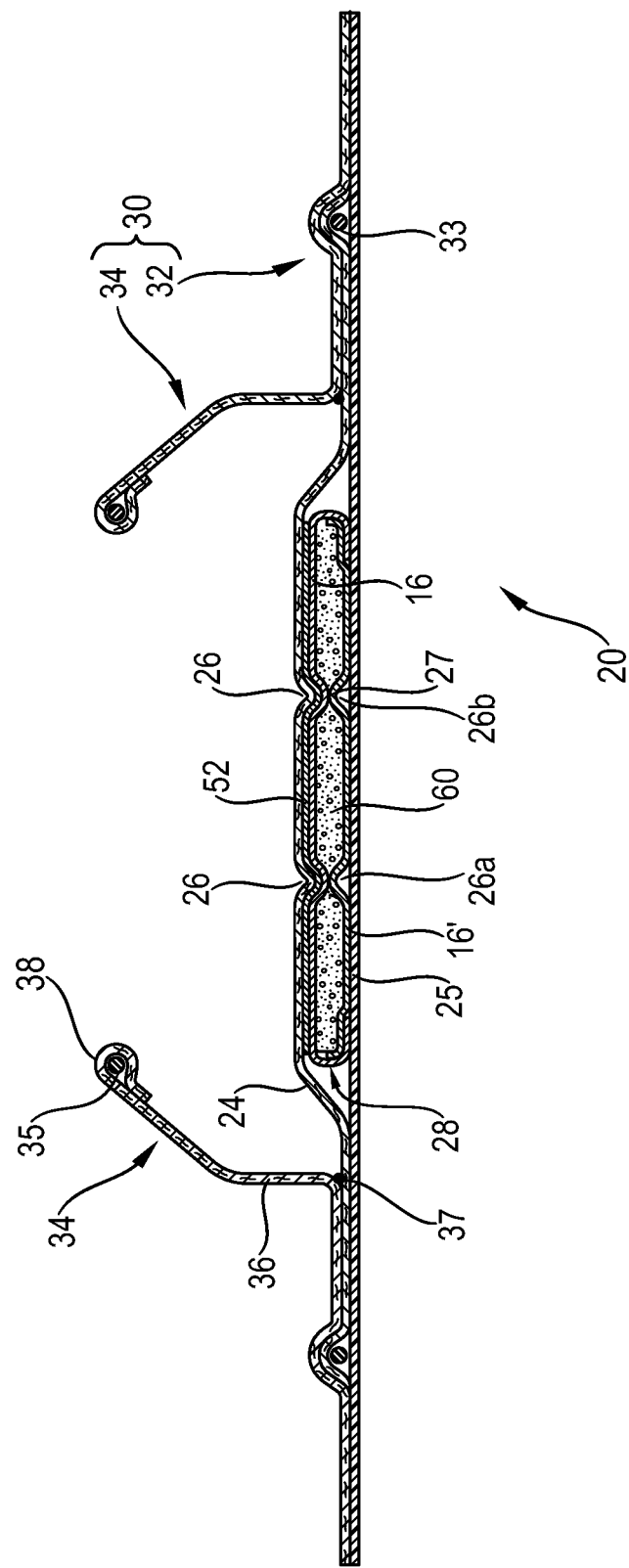
FIG. 3 shows a schematic transversal cross-section of the diaper of FIGS. 1-2 with channels of the first type.
Figure 4:
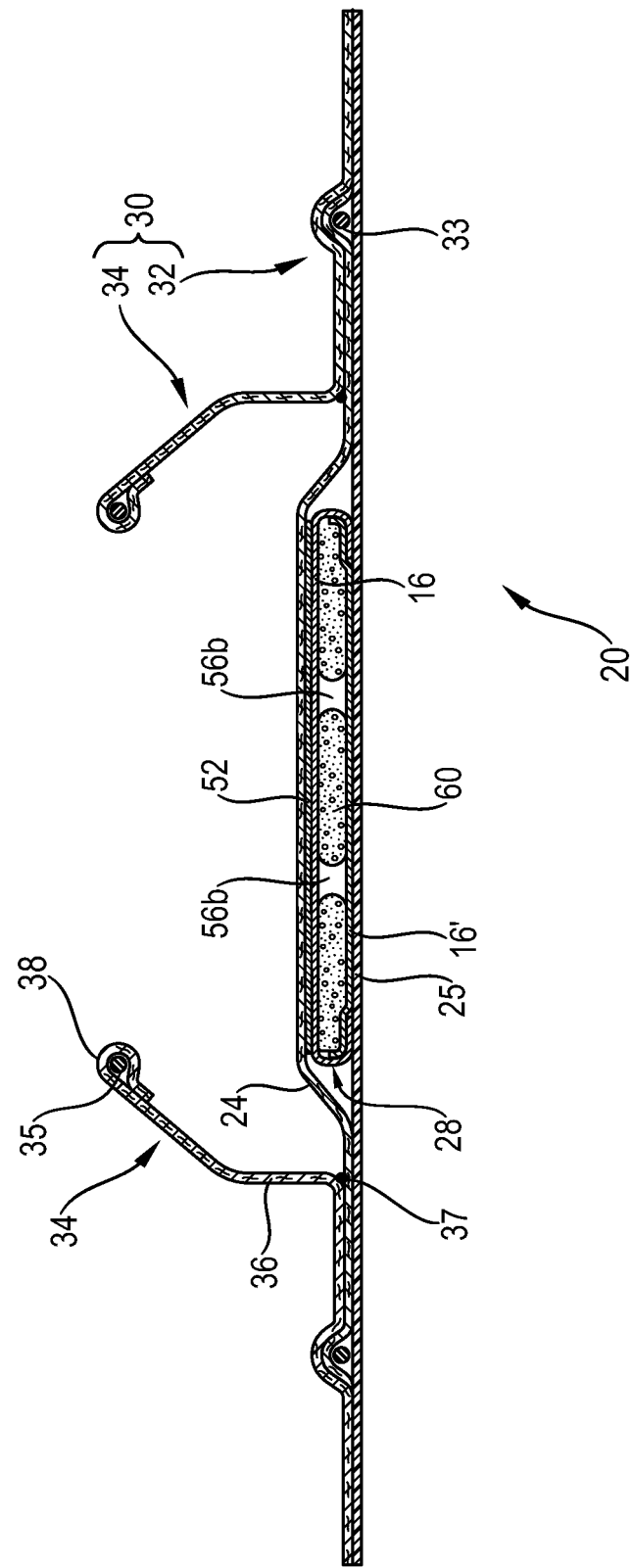
FIGS. 4 and 5 show a schematic transversal cross-section of the diaper of FIGS. 1-2 with channels of the second type.
Figure 5:
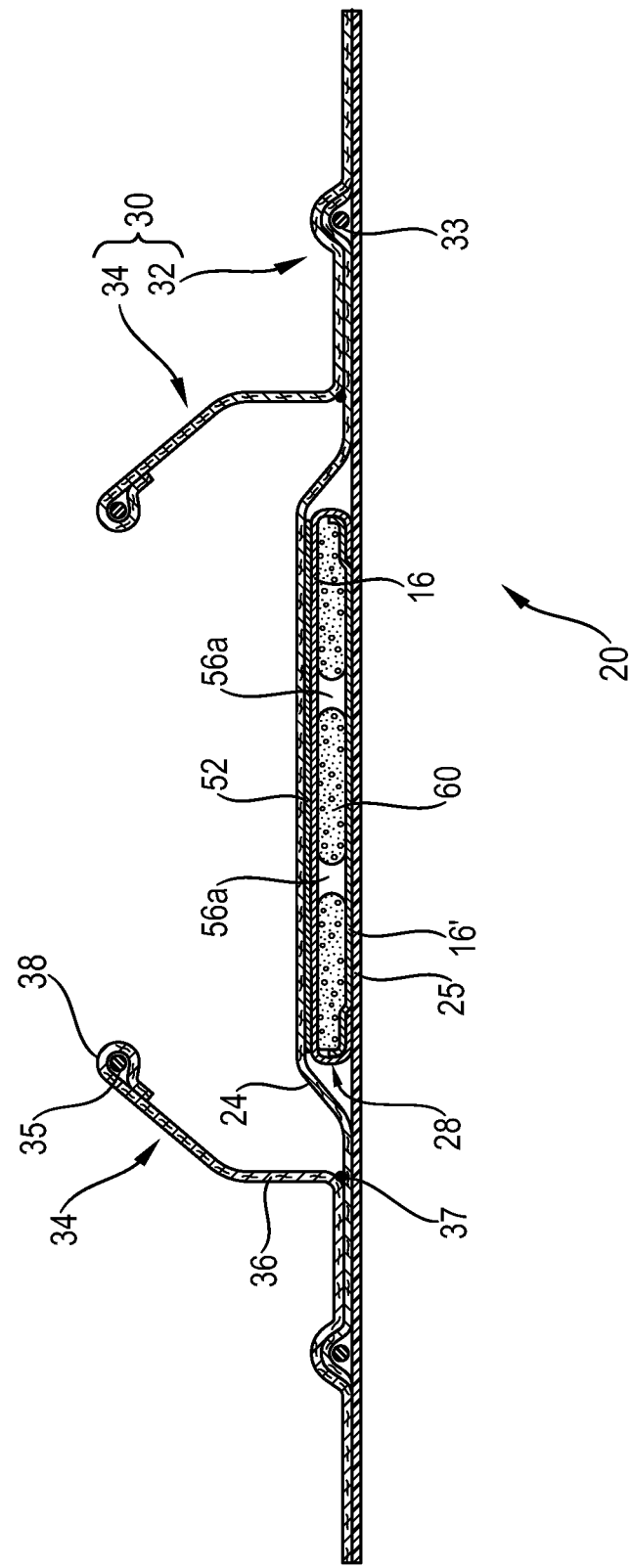

An exemplary absorbent article according to the invention in the form of a baby taped diaper 20 is represented in FIGS. 1-5. FIG. 1 is a top plan view of the wearer-facing side of an exemplary diaper in a flat-out state, with portions of the structure being cut-away to more clearly show the construction of the diaper. FIG. 2 is an exploded view showing the different layers of the diaper of FIG. 1. FIG. 3-5 is transversal cross-sectional view of the diaper 20 taken along lines 3-3, 4-4 and 5-5 of FIG. 1 respectively. This diaper 20 is shown for illustration purpose only, as the invention may be used for making a wide variety of diapers or other absorbent articles such as pant-like diapers, training pants, adult incontinence pants or feminine sanitary pads. In the following description the term diaper and absorbent article are used interchangeably.

As illustrated in FIG. 1, the absorbent article 20 comprises a front edge 10, a back edge 12, and two longitudinally-extending side (lateral) edges 13, 14. The front edge 10 is the edge of the article which is intended to be placed towards the front of the user when worn, and the back edge 12 is the opposite edge. The absorbent article is notionally divided by a longitudinal axis 80 extending along a longitudinal direction from the middle of the front edge to the middle of the back edge of the article and dividing the article in two substantially symmetrical halves relative to this axis, when viewing the article from the wearer-facing side in a flat out configuration, as exemplarily shown in FIG. 1. If some parts of the article are under tension due to elasticized components, the article may be typically flattened using clamps along the periphery of the article and/or a sticky surface, so that the article can be pulled taut so as to be substantially flat. Closed articles such as pant-like baby diapers, training pants for small children, or adult incontinent pants may be cut open along the side seams to apply them on a flat surface, as is known in the art. Unless otherwise indicated, dimensions and areas disclosed herein apply to the article in this flat-out configuration.

As used herein, the terms "comprise(s)" and "comprising" are open-ended; each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essentially of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "preferably", "advantageously", "in particular", "optionally" and the likes also qualify features which are not intended to limit the scope of the claims unless specifically indicated to do so.

The article has further a length L as measured along the longitudinal axis 80 from the back edge 12 to the front edge 10. The absorbent article can also be notionally divided by a transversal axis 90 at half the length L. The transversal axis 90 is perpendicular to the longitudinal axis 80 and placed at half the length of the article. The intersection of the longitudinal axis 80 and the transversal axis 90 is defined herein as the centerpoint C of the article. The article can be further notionally divided in three regions having equal length of a third of L along the longitudinal axis: a front region 62 extending from the front edge 10 towards the crotch region for a third of L, a crotch region 63 in the middle third of the diaper, and a back region 64 extending from the crotch region to the back edge 12 of the article for the remaining third of L. All three regions are of equal length measured on the longitudinal axis, when the article is in such a flat state. The front region, crotch region, back region and longitudinal and transversal axis are defined herein notionally, that is they are typically not materialized in the real diapers, but are useful to describe the positions of various components of the invention relative to each other and the diaper.

The absorbent article 20 comprises a liquid-permeable topsheet 24, a liquid-impermeable backsheet 25 and an absorbent core 28 between the topsheet and the backsheet. The absorbent core comprises an absorbent material 60 enclosed in a core wrap having a top side 16 and bottom side 16'. The absorbent material 60 defines an absorbent layer having deposition area within the core wrap. The absorbent core 28 further comprises within the deposition area defined by the absorbent material 60 at least one channel 26 of a first type, with relatively strong bond 27, and at least one channel of a second type 56 having no bond (as illustrated in the Figures) or at least weaker bonds than the first type of bond. How to achieve these bonds will be discussed further below.

The absorbent article may further comprises one or more intermediate layers between the topsheet and the absorbent core. As illustrated this may be an acquisition layer 52 directly underneath the topsheet. Optionally a distribution layer (not represented) between the acquisition layer 52 and the absorbent core 28 may also be present. Advantageously, the topsheet may be attached directly (or indirectly through an acquisition layer) to the channels of the absorbent core (more precisely the top layer 16 of the core wrap corresponding to the channels) so that the three-dimensionality of the channels is also present on both sides of the diapers in dry and wet state.

The wearer-facing side of the article is principally formed by the topsheet 24. A lotion (not represented) may be present, typically in longitudinally-extending stripes, directly on the topsheet. Other typical diaper components are represented in the Figures, such as elasticized gasketing cuffs 32 (also called outer cuffs), upstanding barrier leg cuffs 34 (inner cuffs). For clarity of the drawings, only one elastic strand 33, 35 is shown for each type of cuff, but typically each cuff may typically comprise from 1 to 4 elastic strands. In taped diapers, a pair of fastening tabs 42 and a landing zone 44 are typically provided. These further components will be discussed in more details further below. The absorbent article may also comprise other typical components, which are not represented in the Figures, such as a back elastic waist feature, a front elastic waist feature, transverse barrier cuffs, a wetness indicator between the backsheet and the absorbent core that changes color when contacted with urine, etc.

General Description of an Absorbent Core 28

Figure 6:
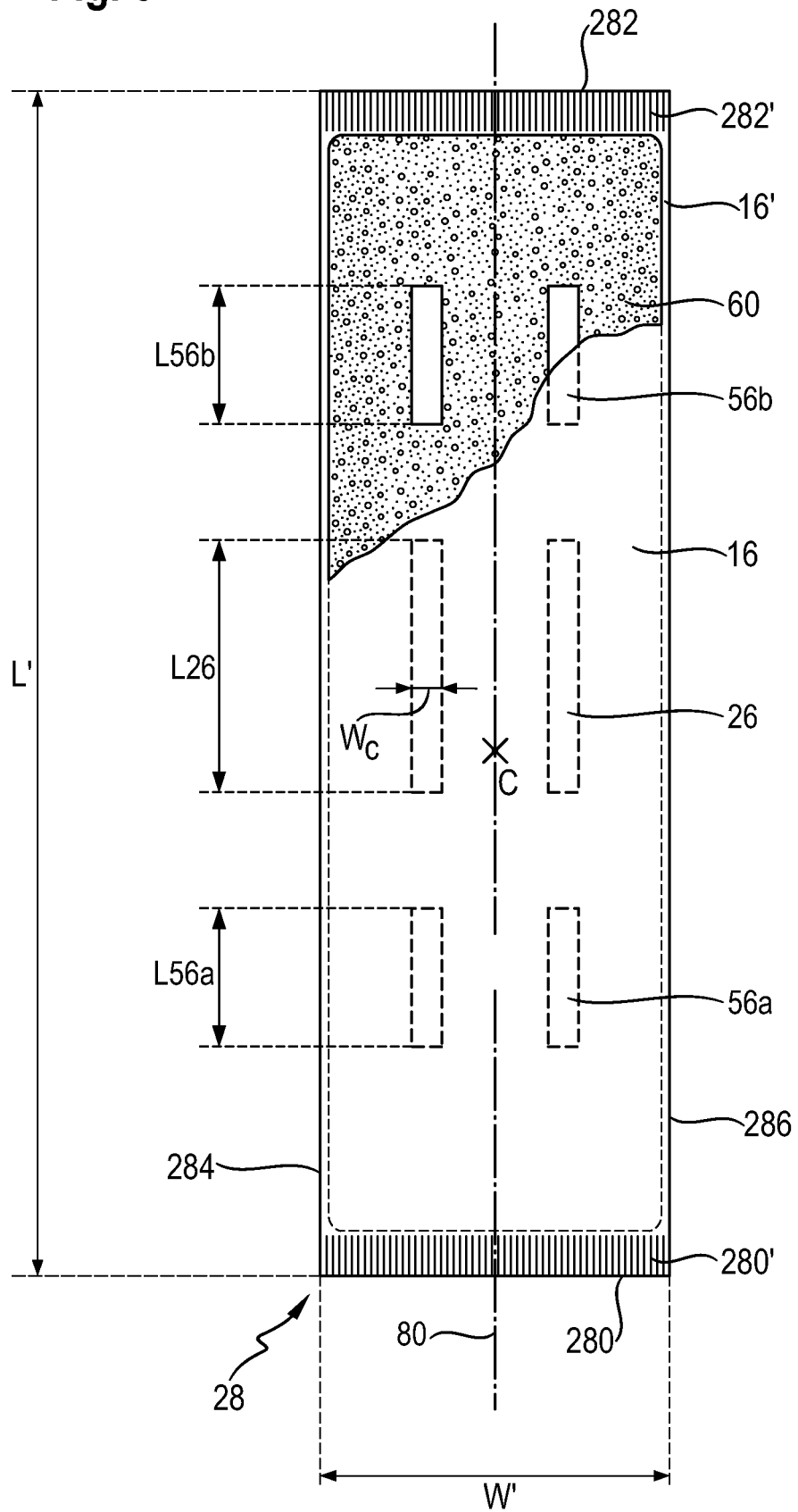
FIG. 6 is a top view of the exemplary absorbent core of the previous Figures shown in isolation and the top side of the core wrap partially removed.
Figure 7:
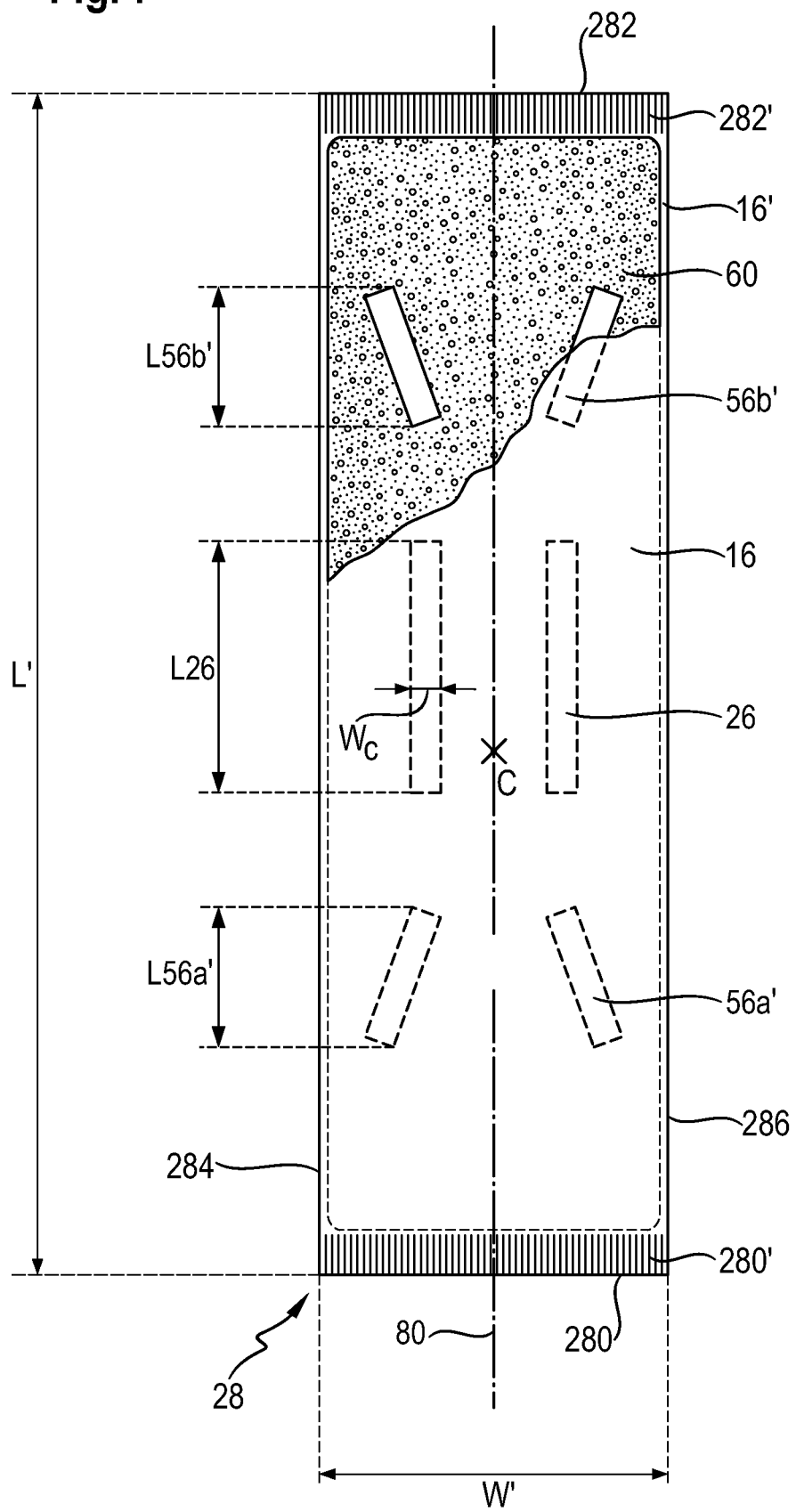
FIG. 7 is a schematic top view of an absorbent core with an alternative channel configuration.

Two exemplary absorbent cores 28 according to the invention are illustrated on FIGS. 6-7 in isolation. As used herein, the term "absorbent core" or "core" refers to a component of an absorbent article which comprises an absorbent material contained in a core wrap. As used herein, the term "absorbent core" does not include the topsheet, the backsheet or a distribution/acquisition layer. The absorbent core has typically the most absorbent capacity of all the components of the absorbent article, and comprises all or at least the majority of superabsorbent polymer (SAP) in the article. The core typically thus consists essentially of, or consists of, the core wrap, the absorbent material and optionally adhesives. The absorbent material comprises a blend of SAP particles and cellulose fibers. The terms "absorbent core" and "core" are herein used interchangeably.

The absorbent core may be typically thin and conformable, so that it can be laid on a flat surface as well as a curved surface, for example the curved surface of a drum during its making process. FIG. 6 shows a top view of the absorbent core of the article of FIGS. 1-5, and FIG. 7 an alternative core having different channel orientations for the second type of channels. The core wrap may comprise two distinct substrates forming respectively the top side 16 and bottom side 16' of the core wrap and attached together, as illustrated in the Figures, but it is also common and possible to have a single substrate forming both top and bottom sides of the core wrap. The absorbent core typically comprises a front edge 280, a back edge 282 and two longitudinally-extending side edges 284, 286 joining the front edge and the back edge. The front edge of the core 280 is the edge placed or intended to be placed towards the front edge 10 of the absorbent article. Typically the absorbent material 60 of the core may be advantageously distributed in somewhat higher amount towards the front edge than towards the back edge as more absorbency is typically required towards the front half of the article. Typically the front and back edges 280, 282 may be shorter than the longitudinally-extending side edges 284, 286. The top side of the core wrap may be treated to be more hydrophilic than the bottom side.

The overall footprint of the absorbent core is typically defined by the core wrap and is typically generally rectangular with a core width W' in the transversal direction and a core length L' in the longitudinal direction as measured from edge to edge, including the region of the core wrap which does not enclose the absorbent material, in particular at the front end seal 280' and the back end seal 282' when present. If the core is not rectangular, the maximum dimension measured along the transversal direction and the longitudinal direction can be used to report the width and length of the core respectively. The width and length of the core may vary depending on the intended usage. For baby and infant diapers, the width W' may for example be in the range from 40 mm to 200 mm and the length L' from 100 mm to 600 mm. Adult incontinence products may have higher maximum dimensions. The absorbent core may be symmetrical relative to its longitudinal axis 80. The longitudinal axis of the core typically overlaps with the longitudinal axis of the absorbent article when the core is incorporated in the article, so both longitudinal axis are designated by the same number 80 in the Figures.

The absorbent material 60 comprises a blend of cellulose fibers with superabsorbent polymer (SAP) particles, also called absorbent gelling materials (AGM), see for example U.S. Pat. No. 5,151,092 (Buell). The amount of SAP is less than 80% by weight relative to the total weight of the absorbent material. The absorbent material in particular comprises, by weight, from 30% to 75% of SAP particles, in particular from 40% to 70% by weight of SAP particles, or from 45% to 65% by weight of SAP particles relative to the total weight of absorbent material. The rest of the absorbent material may typically be cellulose fibers. Thus the amount of cellulose fibers in the absorbent material is at least 20%, more particularly from 25% to 70%, more particularly from 30% to 60%, by weight relative to the weight of the absorbent material of the core. Synthetic fibers may also be comprised in the absorbent core but are not considered as absorbent material unless they have absorbent capacity.

Suitable SAP may be any water-insoluble, water-swellable polymers capable of absorbing large quantities of fluids, as is known in the art. The term "superabsorbent polymer" refers herein to absorbent materials, typically cross-linked polymeric materials, that can absorb at least 10 times their weight of an aqueous 0.9% saline solution as measured using the Centrifuge Retention Capacity (CRC) test (EDANA method WSP 241.2.R3 (12)). The SAP may in particular have a CRC value of more than 20 g/g, or more than 24 g/g, or of from 20 to 50 g/g, or from 20 to 40 g/g, or 24 to 30 g/g.

The absorbent material 60 defines an absorbent material deposition area within the core wrap. The deposition area is delimited by the periphery of the absorbent layer formed by the absorbent material, including the channel areas, as seen from above within the plane of the core. The deposition area may be generally rectangular as shown in the Figure, but it may also be advantageously shaped so that the longitudinal edges 284, 286 of the cores have a tapered section in the crotch region relative to the front region and/or back region, as is known in the art for so-called "shaped cores". Small size baby diapers may also comprise a notch on the front edge of the absorbent material's deposition area to adapt to the presence of remains of the umbilical cord of very small babies.

The absorbent material 60 may be deposited on one side of a core wrap material, with the other side of the core wrap being then applied on top of the absorbent layer thus deposited. The two sides of the core wrap may be made from a single substrate which is folded around the absorbent layer, or alternatively two different substrates may be used to form the first and the second sides of the core wrap respectively. The absorbent cores of the present invention are not limited to a particular process for making them, and the cores of the invention may be made by conventionally air-laying a blend of cellulose fibers and superabsorbent particles on a conventional air-laying drum fitted with raised portions matching the shapes of the desired channels so that that substantially no absorbent material is deposited in these areas. See for example WO2004/011723 (Venturino et al.) for a modified drum having raised portions to create areas having different basis weight. The shape of the raised portions may be adapted to make any desired channel shapes.

The absorbent core may have any caliper. Typically, the caliper of the core (dry, i.e. before use) as measured at the centerpoint point (C) or at any other points of the surface of the core according may range from 2.0 mm to 10.0 mm, in particular from 3.0 mm to 7.0 mm as measured at 2.07 kPa (0.30 psi) with a flat circular foot having a diameter of 17.0 mm (±0.2 mm).

First Type Channels 26 and Second Type Channels 56

The absorbent core 28 comprises at least two channels 26, 56 within the absorbent material's deposition area. The channels may in particular be areas substantially free of absorbent material. "Substantially free" means that some minor amount of absorbent material may be present, however the basis weight of the absorbent material inside the channels represents no more than 25% by weight relative to the average basis weight of the absorbent material in the deposition area (including the channels). For example, if the average basis weight of the absorbent material in the deposition area is 200 gsm, an area encompassed within the deposition area can be considered as a channel if it has a basis weight of absorbent material which is no more than 50 gsm. The basis weight of the absorbent material in the channels is advantageously even lower, in particular no more than 20%, or no more than 10%, relative to the average basis weight of the absorbent material in the deposition area. The channels may be in particular areas completely free of absorbent material (minute amount of absorbent material accidental due to involuntary contamination of the channels due to the high speed of the making process are of course disregarded).

According to the present invention, the absorbent core comprises two different types of channels. The first type of channels 26 comprise a bond 27 between the top side of the core wrap and the bottom side of the core wrap. This bond provides for structural integrity of the channels in dry and wet state. Any known bonding techniques known in the art may be used to provide for this bond, in particular one selected from adhesive bonding, thermo bonding, mechanical bonding, ultrasonic bonding, or any combinations thereof. An adhesive may be for example applied in the areas of the channels on the inner side of the top side and/or the inner side of the bottom side of the core wrap, typically by slot glue application or any other means, followed by the application of pressure in the areas of the channels to provide a good adhesive bonding in these areas. Exemplary patent disclosures of such adhesive bonding processes can be found for absorbent cores in WO2012/170798A1 (Jackels et al.), EP2,905,000 (Jackels et al.) and EP2,905,001 (Armstrong-Ostle et al.).

Other bonding such as thermo bonding, mechanical bonding, ultrasonic bonding can also be used as additional bonding or as an alternative bonding. For example, in the first type of channels an adhesive bonding may be reinforced by a thermo bonding, mechanical bonding or ultra-sonic bonding. Such thermo, mechanical or ultrasonic bonding can be applied on the channel areas through the external sides of the core wrap, see for example WO95/11652 (Tanzer et al.) disclosing secondary bonding comprising a water-resistant adhesive or a thermo bond.

Typically the bonds 27 may generally have the same outline and shape as the channel areas 26 in which they are contained, but may be slightly smaller to allow for a safety margin (e.g. by a few mm) as some deviations from the optimal registration may happen during high speed process. It is expected that channel bonds 27 may be more efficiently made and stronger if they are provided in macroscopic areas with no absorbent material (except of course accidental contamination) compared to bonds provided in areas containing non-negligible absorbent material.

The absorbent core comprises a second type of channels wherein the core wrap is not bonded through the channels, or is at least less bonded than in the first type of channels. This second type of channels with no or weaker bonds provide for an initial quick fluid distribution in the area of the core where they are present. Once the core starts absorbing fluid, these channels of the second type do not restrict the swelling of the absorbent material and can immediately release extra space that can fill up with the expanding absorbent material.

Unbonded channels can be obtained by not providing an adhesive or any other bonding means in the area of the channels of the second type, so that the top side and the bottom side of the core wrap in these area will not bond to each other. This is for example illustrated in FIGS. 4-5 for the channels 56.

Channels of the second type may alternatively have weaker bonds that the channels of the first type. In fact, it is common that an inner core glue (also called auxiliary glue) is present on the inner surface of the substrate forming the top side and/or bottom side of the core wrap. Such inner core glue may be used to at least partially immobilize the absorbent material within the core wrap. The inner core glue is typically applied broadly on at least one side of the core wrap by slot coating in the form of longitudinal stripes or spiral coating on the inner surface of a substrate as is known in the art. Thus in the cases where glue is present within the core wrap, it may be difficult or complex to avoid applying any glue in the relatively narrow zones within the deposition area that correspond to the second type of channels. However, these adhesives will not provide channel bonds or only weak bonds if the adhesive is provided at relatively low basis weight and/or if no or little pressure is applied between the two sides of the core wrap in these regions during the making process of the core. An hotmelt adhesive will also typically cool in a few seconds and loose its adhesive properties, so that if no or little pressure is applied in the channel areas directly after the application, an auxiliary glue or fibrous network hotmelt adhesive will not create a bond or at least a much weaker one than if a strong pressure was applied after a few milliseconds following glue application for example. Alternatively or additionally, more of the same adhesive or a different adhesive (herein reinforcing glue) may be applied in the area of the first type of channels but not in the second type of channels to provide stronger bonds in the first type of channels than in the second type of channels. Alternatively or additionally, additional bonding such as thermo-bonding or ultrasonic bonding may be used in addition to any of the structural adhesives indicated previously in both type of channels.

To sum up, the channels of the first type are intentionally provided with relatively strong bonds, for example by using a first bonding means such as an inner core glue and an additional bonding means such as: additional pressure application to bond both sides of the core wrap and/or a supplementary reinforcing glue specifically for these channels, and/or a thermo-, ultrasonic- or mechanical bonding (such as embossing). The channels of the second types are on the other hand not provided with any bonds, or if bonds are present these bonds are not provided with the additional bonding means of the first type of bonds. The channel bonds of the second type if they are present will thus more easily delaminate than the bonds of the first types of channels.

The strength of the bonding between both sides of the core wrap in a channel can be characterized by its Static Peel Force Time. In summary, this parameter measures the time in minutes it takes for a 1-inch wide sample to delaminate when one side of the sample is hanging with a 150 g weight attached to it. The first Static Peel Force Time is higher than the second Static Peel Force Time.

In a first aspect, the first Static Peel Force Time is more than 50 minutes and the second Static Peel Force Time is less than 50 minutes. The first Static Peel Force Time may also be more than 60 minutes and/or more than 70 minutes. This means that at least one of the channel has Static Peel Force Time above 50 minutes, but of course there may be more than one channels having a Static Peel Force Time of more than 50 minutes, for example a pair of such channels, or three, or four channels or more. All these channels do not need to have the exact same Static Peel Force Time to qualify as channels of the first type, as long as their individual Static Peel Force Time is more than 50 minutes, in particular more than 60 minutes or more than 70 minutes. Likewise, at least one channel has a Static Peel Force Time of less than 50 minutes, but it is of course possible that more than one channel, in particular a pair, or three, or four, or more channels have individual Static Peel Force Time of less than 50 minutes, in particular less than 40 minutes, or less than 35 minutes, or any values ranging from 0 minute to less than 30 minutes. All these channels do not need to have the exact same Static Peel Force Time to qualify as channels of the second type as long as their individual value are sufficient low. The second Static Peel Force Time may even be zero for one or more of the channels of the second type, meaning that this channel of the second type are not or only very weakly bonded so that they open immediately.

In a second aspect, the first Static Peel Force Time may be at least 10% higher than the second Static Peel Force Time. In particular, the first Static Peel Force Time may be at least 20% higher than the second Static Peel Force Time, more particularly the first Static Peel Force Time may be at least 30% greater than the second Static Peel Force Time. If the second Static Peel Force is 0, in such as case the minimum value of the first Static Peel Force Time may be at least 10 minutes, in particular at least 20 minutes or at least 30 minutes.

In a third aspect, the first Static Peel Force Time is at least 20 minutes greater than the second Static Peel Force Time. In particular, the first Static Peel Force Time may be at least 30 minutes greater than the second Static Peel Force Time, more particularly the first Static Peel Force Time may be at least 40 minutes greater than the second Static Peel Force Time. Of course the channels of the invention can advantageously combine any of the first, second and third aspects, for example the first and second, or the first and the third or the first and the second.

The channels of the first type and the second type may be generally formed in the same manner, except for the bonding step for the first type of channels, which does not exist or is much weaker than in the second type of channels. Thus the channels of the first type can potentially have the same general shape and placement as the channels of the second type. Herein, when the term "channels" is used without further indication, it is meant any or all of the "channels of the first type and/or channels of the second type", unless it is clear from the context that a particular type of channels was meant.

It is advantageous in terms of side leakage prevention that all, or at least some of, the channels do not extend to any of the edges of the deposition area formed by absorbent material layer. In other words at least one of the channels of each type may be advantageously completely encompassed within the deposition area formed by the absorbent material. The channels in the core may in particular end at a distance of at least 5 mm from any outer edges of the absorbent layer's deposition area. The channels of the first type and the channels of the second may be separated from each other by a separating zone or buffer comprising absorbent material, as represented in FIGS. 6-7. The minimal distance between channels of the first type and the channels of the second type may be for example at least 5 mm, in particular at least 10 mm. This can help avoiding that fluid collected in the channels of the first type are conducted immediately in the channels of the second type and so that these would prematurely disappear at the first gush of insulting liquid, especially when the channels of the first type are in the crotch region of the article. It is however not excluded that some or all of the channels of the second type may also be connected to the channels of the first type.

Channels of each type may be disposed as one or more pair of channels symmetrically disposed relative to the longitudinal axis, so that the channels of the first type are mirror image of each other relative to the longitudinal axis, and likewise the channels of the second type are mirror image of each other relative to the longitudinal axis. This typically provides for better fit and fluid distribution than if the channels were randomly or non-symmetrically disposed. It is not excluded that the pair of channels may be joined together at their front and/or back extremities.

The channels are typically longitudinally-extending, meaning that each channel extends at least as much in the longitudinal direction than in the transversal direction, and typically at least twice as much in the longitudinal direction than in the transverse direction (as measured after projection on the respective longitudinal and transversal axis). One or more of the channels may have a length to height ratio (CL/CH) that ranges from 2 to 20, in particular from 4 to 15 see for example EP2,979,671A1 (Kreuzer et al.) for example of channels with such ratio and how to calculate them. At least some the channels may have a length Lc projected on the longitudinal axis 80 that is at least 2% of the length L' of the absorbent core, in particular from 5% to 30% of the core length L'. At least some the channels may have a width Wc along at least part of their length which is at least 2 mm, or at least 3 mm or at least 4 mm, up to for example 20 mm, or 16 mm or 12 mm. The width Wc for each channel may be constant through substantially its whole length or may vary along its length. For example the channels may be straight and longitudinally oriented with the width gradually decreasing or increasing from front to back of the article. The width of the channels may be the same or different between different channels.

Looking more closely at the exemplary core shown in a top view in isolation on FIG. 6, this core example has a first pair of first type channels 26 toward the longitudinal middle of the core, a first pair of second type channels 56a towards the front 280 of the core, and a second pair of second type channels 56b towards the back 282 of the core. The absorbent core may alternatively comprise only one pair of second type channels either in the front or back. Of course an absorbent core according to the invention may comprise more or less channels than represented in the illustration.

More generally, it may be advantageous that at least one channel, in particular a pair of channels, of the first type is at least partially present in the crotch region 63 of the article and optionally extend into the front region 62 and/or the back region 64 of the article. This is believed to provide for a better wet fit of the absorbent article. In addition or alternatively, at least one, in particular a pair, of the second type of channels 56a may be at least partially present in the front region of the article, and/or at least one, in particular a pair, of the second type of channels 56*b* may be at least partially present in the back region of the article. These channels of the second type are useful as indicated previously to provide for early distribution of the fluid when the absorbent core starts to absorb fluid.

The channels in FIG. 6 are all straight and oriented longitudinally. However different shape and orientation of the channels are possible. For example at least some of the channels may be curved. In particular some of the channels may be concave towards the longitudinal axis 80, as in inverted brackets) (in particular at least the channels of the first type present in the crotch region. Example of such curved channels of the first type are illustrated in a non-limiting manner in WO2012/170779 (Rosati et al.). Any of the channels may have an arcuate portion facing the longitudinal axis, and an angle between a tangent line of the arcuate portion and the longitudinal axis is greater than or equal to 20 degrees. Channels with an arcuate portion are for example disclosed in WO2014/093130A1 (Roe et al.).

Some of the channels may also be straight but at an angle relative to the longitudinal axis, for example up to 60°, or up to 40° relative to a line parallel to the longitudinal axis. This is for example illustrated on FIG. 7 for the two pairs of second type channels 56'*b* and 56'*a*. The channels may have other shape or orientation as those indicated above. For example the channels may be branched, or U shaped, and/or form a pocket towards the back of the article, especially for bonded channels of the first type, as exemplarity disclosed in WO2014/093129A (Roe et al.). There may or may not be a channel that partially extends longitudinally and coincides with the longitudinal axis of the article, however such a channel may create a folding line in the middle of the article that may cause the article to fold downwards which may cause some loss of contact. When present as one ore symmetrical pair(s) relative to the longitudinal axis, the channels be spaced apart from one another over part of or their whole longitudinal dimension. The spacing distance may be at some points or over the whole length of the channels for example at least 5 mm, or at least 10 mm, or at least 16 mm as measured in the transversal direction. Some channels are present as a pair may be also joined at their base as in a U-shape or V-shape, or may be joined towards their middle to form a cross or X-shape.

Taken as a whole, the cumulated length of all the channels projected on the longitudinal axis (without counting double for any overlap in case two channels, such as a pair of channels, are positioned at an overlapping position on the longitudinal axis) may represent from 10% to 80% of the full length of the article L. For example, on FIG. 6, the cumulative length of the channels is L56b+L26+L56a (the length of the channels of the first type in the crotch region, plus the length of the channels of the second type in the back region, plus the length of the channels of the second type in the front region). Likewise on FIG. 7, the cumulative length of the channels is L56'b+L26+L56'a. The cumulative projected length of the channels divided by the length of the article L and expressed in percentage may thus range from 10% to 80%, or 20% to 70%, in particular from 10% to 30%, or from 30% to 70%.

Core Wrap 16, 16'

The absorbent core comprises a core wrap which encloses the absorbent material. The core wrap can typically comprise a substrate for receiving the absorbent material when the core is made. Various core wrap constructions are possible. The core wrap may in particular comprise as represented in the Figures two separate substrates 16, 16' forming the top side and the bottom side of the core wrap respectively. Having two different substrates for example allows more easily depositing an inner core glue on both the inner surface of the top side and the inner surface of the bottom side of the core wrap before combining these substrates to form the core wrap. The two substrates may be attached in a C-wrap or sandwich configuration with two longitudinal seals 284', 286', and optionally a front seal 280' and a back seal 282'. However this core wrap construction is not limiting of the invention, as any conventional core wrap construction may also be used, for example a single substrate on a portion of which the absorbent material is deposited and then the rest of the substrate folded over the deposited absorbent material to form the other side of the core. This single substrate construction can then be sealed longitudinally with a single longitudinal edge seal. The core wrap may also comprise two substrates disposed flat in a face to face relation (sandwich) with longitudinal side seals along their longitudinal sides.

The core wrap material may be any materials suitable for receiving and containing the absorbent material. Typical substrate materials used in the production of conventional cores may be used, in particular paper, tissues, films, wovens or nonwovens, or laminate of any of these. The core wrap may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US 2011/0268932A1, US2011/0319848A1 and US2011/0250413A1. Nonwoven materials are typically made of synthetic fibers, such as PE, PET and in particular PP fibers. It is also possible than the core wrap may be at least partially formed from a component of the article having another function than merely serve as a substrate for the absorbent material. For example, it is possible that the backsheet may form the bottom side of the core wrap and/or that a distribution layer or the topsheet may form the top side of the core wrap. However, typically the core wrap is made of one or more substrates whose only or main function is to receive and enclose the absorbent material, as indicated previously.

As used herein, the terms "nonwoven layer" or "nonwoven web" generally means a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or synthetic origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as melt-blowing, spunbonding, solvent spinning, electrospinning, carding and airlaying. The basis weight of nonwoven webs is usually expressed in grams per square meter ($g/m^2$ or gsm).

As illustrated in FIGS. 4-5, a first substrate 16 may substantially form the whole of the top side of the core wrap and a second substrate 16' substantially form the whole of the bottom side of the core wrap, but it is not excluded that this may be the other way round. By "substantially forming the whole of the surface", it is meant that if present, the outwardly extending flaps of the other substrate that have been folded longitudinally may also form part of the surface considered. The first substrate 16 may comprise two side flaps laterally extending along the length of the core and which are folded inwardly over each side edge 284, 286 of the absorbent core and the flaps may be attached to the outer surface of the second substrate 16' for example by using an adhesive seal along each C-wrap seal 284', 286'. One or two continuous or semi-continuous lines of glue may be typically applied along the length of the flaps to bond the inner surface of the flaps to the external surface of the other substrate. The reverse construction may of course also be used with the bottom substrate forming flaps over the top substrate.

The core may also comprise so-called sandwich seals where the two substrates are bonded along one edge of the core to each other in face-to-face relationship with the inner surface of each substrate bonded to the inner surface of the other substrate. These sandwich seals can for example be formed using a hotmelt glue applied in a series of stripes in a direction perpendicular to the front and back edges 280, 282 of the core. These end seals 280', 282' are however optional as many absorbent cores are left open at the front and back ends. The longitudinal edges may also be bonded by such a sandwich seal.

Inner Core Glue

An inner core glue between the top side and bottom side of the core wrap is optional but advantageous. The inner core glue can improve the adhesion between the inner surfaces of the core wrap and the absorbent material. The inner core glue may also at least partially form the bonds 27 between the two sides of the core wrap for the first type of channels. The inner core glue may also be responsible for some bonding in the second type of channels, if these have any bond at all. The core wrap may be locally pressed together on the areas of the first channels while the glue is still hot to increase the strength of the adhesive bonding in these areas.

When present, the inner core glue may be applied directly over the inner surface of the top side and/or the inner surface of the bottom side of the core wrap to an area at least partially (e.g. at least 50% and up to 100%) corresponding to the deposition area of the absorbent material to at least partially immobilize the absorbent material. The inner core glue may be applied according to any known techniques, in particular it may be applied as a series of longitudinally extending slots of glue as is known in the art, alternatively by other non-contact applicators such as spiral glue applicators, before the absorbent material is deposited on the nonwoven. The inner glue may thus be present in particular between the absorbent material and the inner surface of the bottom side of the core wrap, and/or between the absorbent material and the inner surface of the top side of the core wrap. An example of partial coverage of the deposition area by an inner core glue (also called auxiliary glue) to immobilize the absorbent material and to form channel bonds is for example disclosed in EP2,886,092 (Stelzig et al.). A fibrous thermoplastic material may also be present within the core wrap to help immobilizing the AGM particles, especially if the core is free of cellulose fibers.

Pant-Like Articles

As indicated previously, the invention may be also used in absorbent articles presented in the form of a pant or underwear (herein "pant"). In these articles, the waist and the leg openings are pre-formed during manufacture so that the article can be put on like underwear. These pant articles typically have a front waist panel and a back waist panel which are sealed together via side seams. The side seams can be broken to remove and discard the article and are typically not re-fastenable. The front and back waist panels are typically elasticized. Pants are used as taped diapers on babies and younger children for day wear and for overnight dryness, as training pant for older children at the toilet training stage, and also as adult incontinence protection.

Pant-like articles typically comprise a front waist panel and a back waist panel joined together via side seams to form the waist opening and at least part of the leg openings. The waist panels are typically elasticized, either using a material which is inherently elastic to make them (such as a laminate comprising an elastomeric layer between two nonwoven layers) or by sandwiching a plurality of elastic strands between two nonwovens along the width of the panels, as is known in the art. The pants also typically comprises a chassis comprising the remaining components of the article, in particular the topsheet, the backsheet, the absorbent core and barrier cuffs including upstanding barrier leg cuffs and attached on one side to the front waist panel and on the other side of the back waist panel. These components may be generally constructed as in previously disclosed for the taped diaper.

Having described in details the key features of the invention, the following sections provide more details on some of the typical components found in absorbent articles. The materials described below are of course optional and non-limiting, unless explicitly indicated otherwise.

Topsheet 24

The topsheet typically forms the majority of the wearer-contacting surface of the article and is the first layer that the body exudates contact. The topsheet is preferably compliant, soft-feeling, and non-irritating to the wearer's skin. Further, at least a portion of the topsheet is liquid permeable, permitting liquids to readily penetrate through its thickness. Any known topsheet may be used in the present invention. A suitable topsheet may be manufactured from a wide range of materials. Most topsheets are nonwoven materials or apertured formed films, but other materials are possible such as porous foams, reticulated foams, woven materials. Typical diaper topsheets have a basis weight of from about 10 gsm to about 28 gsm, in particular between from about 12 gsm to about 18 gsm but higher basis weights are possible if it is desired to provide a very soft feeling wearer-contacting surface for example.

Nonwoven topsheets may be made of natural fibers (e.g., wood or cotton fibers), synthetic fibers or filaments (e.g. polyester or polypropylene or bicomponent PE/PP fibers or mixtures thereof), or a combination of natural and synthetic fibers. If the topsheet includes nonwoven fibers, the fibers may be spunbond, carded, wet-laid, meltblown, hydroentangled, or otherwise processed as is known in the art. In particular the topsheet may be a spunbond PP nonwoven. A suitable topsheet comprising a web of staple-length polypropylene fibers is manufactured by Veratec, Inc., a Division of International Paper Company, of Walpole, Mass. under the designation P-8.

The topsheet may be of the type comprising a plurality of apertures. At least some of the apertures may have an area ranging from 1 $mm^2$ to 20 $mm^2$, and the topsheet may in particular comprise on average from 1 to 20 apertures per $cm^2$. The aperture ratio (the surface of all the apertures divided by the overall surface of the topsheet, measured when the topsheet is in a relaxed state, i.e. with just enough tension to smooth out any wrinkles) is advantageously in the range from 10% to 45%, in particular from 25% to 40%, more particularly from 30% to 35%. Typically, the total area of the apertures at the surface of a diaper may have an area of between about 10 cm$^2$ and about 50 cm$^2$, in particular between about 15 cm$^2$ and 35 cm$^2$. Examples of apertured topsheet are disclosed in U.S. Pat. No. 6,632,504 (Gillespie et at.).

WO 2011/163582 (Rinnert et al.) also discloses a suitable colored nonwoven topsheet having a basis weight of from 12 to 18 gsm and comprising a plurality of bonded points. Each of the bonded points has a surface area of from 2 mm$^2$ to 5 mm$^2$ and the cumulated surface area of the plurality of bonded points is from 10 to 25% of the total surface area of the topsheet.

Suitable formed film topsheets are also described in U.S. Pat. Nos. 3,929,135, 4,324,246, 4,342,314, 4,463,045, and 5,006,394. Other suitable topsheets may be made in accordance with U.S. Pat. Nos. 4,609,518 and 4,629,643. Such formed films are available from The Procter & Gamble Company of Cincinnati, Ohio as "DRI-WEAVE" and from Tredegar Corporation, based in Richmond, Va., as "CLIFF-T". The topsheet may also have a three-dimensional appearance and feel, or there may be an additional, smaller, three-dimensional layer placed on top of the topsheet. Such three-dimensional additional layers may be for example particularly useful to receive low viscous exudates such as the stool of young babies. Examples of such fluid entangled dual layered three-dimensional materials and processes to obtain them have been disclosed for example in US2014/0121623A1, US2014/0121621A1, US2014/0121624A1, US2014/0121625A1.

The topsheet may also be treated with a wetting agent to make it more hydrophilic. The wetting agent may be a surfactant as is known in the art. Other possible treatments are for example special coating by nanoparticles, as for example described in U.S. Pat. Nos. 6,645,569, 6,863,933, US2003/148684 and US2005/008839 (Cramer et al.) and U.S. Pat. No. 7,112,621 (Rohrbaugh et al). Any portion of the topsheet may also coated with a lotion as is known in the art. Examples of suitable lotions include those described in U.S. Pat. Nos. 5,607,760, 5,609,587, 5,643,588, 5,968,025 and 6,716,441. The topsheet may also include or be treated with antibacterial agents, some examples of which are disclosed in WO95/24173. Further, the topsheet, the backsheet or any portion of the topsheet or backsheet may be embossed and/or matte finished to provide a more cloth like appearance.

Backsheet 25

The backsheet may be any backsheet known in the art for absorbent articles. The backsheet may be positioned directly adjacent the garment-facing surface of the absorbent core. The backsheet prevents, or at least inhibits, the exudates absorbed and contained therein from soiling articles such as bedsheets and undergarments. The backsheet is typically impermeable, or at least substantially impermeable, to liquids (e.g., urine). The backsheet may, for example, be or comprise a thin plastic film such as a thermoplastic film having a thickness of about 0.012 mm to about 0.051 mm. The basis weight of those films is usually as low as possible to save material costs, typically from 10 gsm to 30 gsm, in particular below 20 gsm. A covering low basis weight nonwoven may be attached to the external surface of the film to provide for a softer touch.

Suitable backsheet materials include breathable materials which permit vapors to escape from the absorbent article while still preventing, or at least inhibiting, exudates from passing through the backsheet. Example breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097.

The film may include at least about 10 weight percent filler particles, for example filler particles that include calcium carbonate, so that wherein the film has been stretched in the machine direction, e.g. to at least about 150 percent, fractures are formed where said filler particles are located. The films may be biaxially stretched at least about 150 percent in the machine direction and a transverse direction to cause fractures to form where said filler particles are located. Breathable films may generally have Water Vapor Transmission Rates (WVTR) in excess of 300 grams per square meter per 24 hours. The WVTR may be measured by the Desiccant Method as indicated in ASTM E96/E96M-14.

U.S. Pat. No. 6,075,179 for example discloses a suitable multilayer film comprising: a core layer made from an extrudable thermoplastic polymer, the core layer having a first exterior surface and a second exterior surface, a first skin layer attached to the first exterior surface of said core layer to form the multilayer film, the multilayer film defining an overall thickness. The first skin layer defines a first skin thickness, and comprising less than about ten percent of said overall thickness. The overall thickness is not exceeding about 30 micrometers and the multilayer film is a liquid barrier and has a WVTR of at least 300 g/m2/24 hours.

The backsheet may further typically comprise a nonwoven on its most external side to improve softness. Exemplary laminates comprising a breathable film and a nonwoven layer are for example disclosed in WO2014/022,362A1, WO2014/022,652A1 and U.S. Pat. No. 5,837,352. The nonwoven web may in particular comprise a spunbond nonwoven web and/or a laminate of a spunbond nonwoven web and a meltblown nonwoven web. The laminate may also have a water vapor transmission rate of at least 300 g/m2/24 hours. U.S. Pat. No. 5,843,056 for example discloses substantially liquid impermeable, vapor permeable composite backsheet.

Acquisition Layer 52

The absorbent article may advantageously comprise an acquisition layer 52, sometimes referred to as secondary topsheet, whose function is to quickly acquire the fluid away from the topsheet so as to provide a good dryness for the wearer. The acquisition layer is typically placed directly under the topsheet. There may be optionally a distribution layer (not represented) at least partially disposed under the acquisition layer 52. The acquisition layer may typically be or comprise a non-woven material, for example a SMS or SMMS material, comprising a spunbonded, a melt-blown and a further spunbonded layer, but many other alternatives material are known in the art and may be used instead in particular a cared nonwoven. Nonwovens have the advantage that they can be manufactured outside the converting line and stored and used as a roll of material. The nonwoven material may be latex bonded. Exemplary upper acquisition layers are disclosed in U.S. Pat. No. 7,786,341. Carded, resin-bonded nonwovens may be used, in particular where the fibers used are solid round or round and hollow PET staple fibers (50/50 or 40/60 mix of 6 denier and 9 denier fibers). An exemplary binder is a butadiene/styrene latex. Further useful nonwovens are described in U.S. Pat. No. 6,645,569 (Cramer et al.), U.S. Pat. No. 6,863,933 (Cramer et al.), U.S. Pat. No. 7,112,621 (Rohrbaugh et al.), US2003/

148684 (Cramer et al.) and US2005/008839 (Cramer et al.). The acquisition layer may be stabilized by a latex binder, for example a styrene-butadiene latex binder (SB latex). Processes for obtaining such latices are known, for example, from EP 149880 (Kwok) and US 2003/0105190 (Diehl et al.). The binder may typically be present in the acquisition layer in amount ranging from about 12% to about 50%, for example about 30%, by total weight of the acquisition layer. SB latex is available under the trade name GENFLO™ 3160 (OMNOVA Solutions Inc.; Akron, Ohio).

Another typical acquisition layer may be a bonded carded web, in particular a through-air bonded carded web ("TABCW"). "Bonded carded web" refers to webs that are made from staple fibers that are sent through a combing or carding unit, which breaks apart and aligns the staple fibers in the machine direction to form a generally machine direction-oriented fibrous nonwoven web. This web is then drawn through a heated drum, creating bonds throughout the fabric without applying specific pressure (thru air bonding process). A TABCW material provides a low density, lofty through-air bonded carded web. The web may for example have a specific weight basis level at about 15 gsm to about 120 gsm (gram per square meter), in particular about 30 gsm to about 80 gsm. A TABCW material can for example comprise about 3 to about 10 denier staple fibers. Examples of such TABCW are disclosed in WO2000/71067 (KIM DOO-HONG et al.). TABCW are available directly from all usual suppliers of nonwoven webs for use in absorbent articles, for example Fitesa Ltd or Fiberweb Technical Nonwovens.

A further acquisition layer (not shown) may be used in addition to the first acquisition layer described above. For example a tissue layer may be placed between the first acquisition layer and a distribution layer. The tissue may have enhanced capillarity distribution properties compared to the acquisition layers described above. The tissue and the first acquisition layer may be of the same size or may be of different size, for example the tissue layer may extend further in the back of the absorbent article than the first acquisition layer. An example of a hydrophilic tissue is a 13 to 15 gsm high wet strength tissue made of cellulose fibers from supplier Havix.

Fastening System 42, 44

The absorbent article may include a fastening system, especially when the article is a taped diaper as exemplified in FIG. 1. The fastening system can be used to provide lateral tensions about the circumference of the absorbent article to hold the absorbent article on the wearer. Such a fastening system is not necessary for pant articles such as training pants and adult incontinence pants since the waist region of these articles is already bonded and elasticized. The fastening system usually comprises a fastener 42 such as tape tabs, hook and loop fastening components, interlocking fasteners such as tabs & slots, buckles, buttons, snaps, and/or hermaphroditic fastening components, although any other known fastening means are generally acceptable. A landing zone 44 is normally provided on the front waist region of the article for the fastener 42 to be releasably attached. Some exemplary surface fastening systems are disclosed in U.S. Pat. Nos. 3,848,594, 4,662,875, 4,846,815, 4,894,060, 4,946,527, 5,151,092 and 5,221,274 (Buell). An exemplary interlocking fastening system is disclosed in U.S. Pat. No. 6,432,098. The fastening system may also provide a means for holding the article in a disposal configuration as disclosed in U.S. Pat. No. 4,963,140 (Robertson et al.) The fastening system may also include primary and secondary fastening systems, as disclosed in U.S. Pat. No. 4,699,622 to reduce shifting of overlapped portions or to improve fit as disclosed in U.S. Pat. Nos. 5,242,436, 5,499,978, 5,507,86, and 5,591,152.

Front and Back Ears 46, 40

The absorbent article may comprise front ears 46 and back ears 40 as is known in the art in taped diapers. Absorbent articles in pant chassis are already sealed along the waist edges typically do not require front ears and back ears. The ears can be integral part of the chassis, for example formed from the topsheet and/or backsheet as side panel. Alternatively, as represented in FIG. 1, they may be separate elements attached by gluing and/or heat embossing. The back ears 40 are optionally stretchable to facilitate the attachment of the tabs 42 on the landing zone 44 and maintain the taped diapers in place around the wearer's waist. The front ears 46 may also be optionally elastic or extensible to provide a more comfortable and contouring fit.

Barrier Leg Cuffs 34 and Gasketing Cuffs 32

Absorbent articles such as taped diapers, training pants or adult incontinence pants may typically further comprise cuff components 30 that improve the fit of the article around the legs of the wearer. Such cuffs typically comprise barrier leg cuffs 34 and gasketing cuffs 32. The cuffs 30 may comprise a piece of material, typically a nonwoven, which is one side partially bonded to the article and on the other side can be partially raised away from the topsheet and thus stand up from the plane defined by the topsheet as shown for example in FIG. 3. Both parts of the cuffs may be advantageously elasticized. The raised part of the cuff components is referred to herein as barrier leg cuffs 34 and can provide improved containment of liquids and other body exudates approximately at the junction of the torso and legs of the wearer. The barrier leg cuffs 34 extend at least partially between the front edge and the back edge of the absorbent article on opposite sides of the longitudinal axis and are at least present adjacent to the center point C of the article.

The barrier leg cuffs 34 may be delimited by a proximal edge 37 joined to the rest of the article, typically the topsheet, and a free terminal edge 38 intended to contact and form a seal with the wearer's skin. The barrier leg cuffs 34 may be joined at the proximal edge 37 with the chassis of the article by a bond which may be made for example by adhesive bonding, fusion bonding or combination of known bonding means, for example as disclosed in WO2014/168810A1 (Bianchi et al.). The bond at the proximal edge 37 may be continuous or intermittent.

The barrier leg cuffs 34 can be integral with (i.e. formed from) the topsheet or the backsheet, or more typically be formed from a separate material joined to the rest of the article. Typically the material of the barrier leg cuffs may extend through the whole length of the article but is "tack bonded" to the topsheet towards the front edge and back edge of the article so that in these sections the barrier leg cuff material remains flush with the topsheet. Each barrier leg cuff 34 may comprise one, two or more elastic strings 35 close to its free terminal edge 38 to provide a better seal.

In addition to the barrier leg cuffs 34, the article may comprise gasketing cuffs 32, which are formed in the same plane as the chassis of the absorbent article, in particular may be at least partially enclosed between the topsheet and the backsheet, and typically placed further laterally outwardly relative to the barrier leg cuffs 34. The gasketing cuffs 32 can provide a better seal around the thighs of the wearer. Usually each gasketing leg cuff 32 will comprise one or more elastic string or elastic element 33 comprised in the chassis of the diaper for example between the topsheet and backsheet in the area of the leg openings. Typically the barrier leg cuffs 34 are disposed more internally than the gasketing cuffs 32. The barrier leg cuffs are thus also referred to as inner cuffs and the gasketing cuffs as outer cuffs.

For example, U.S. Pat. No. 3,860,003 describes a disposable diaper which provides a contractible leg opening having a side flap and one or more elastic members to provide an elasticized leg cuff (a gasketing cuff). U.S. Pat. No. 4,808,178 (Aziz) and U.S. Pat. No. 4,909,803 (Aziz) describe disposable diapers having "stand-up" elasticized flaps (barrier leg cuffs) which improve the containment of the leg regions. U.S. Pat. No. 4,695,278 (Lawson) and U.S. Pat. No. 4,795,454 (Dragoo) describe disposable diapers having dual cuffs, including gasketing cuffs and barrier leg cuffs. All or a portion of the barrier leg and/or gasketing cuffs may be treated with a lotion.

Distribution Layer

The article may comprise a further intermediate layer between the topsheet and the absorbent core, which will be referred herein as a distribution layer. The function of a distribution layer is to spread an insulting fluid liquid over a larger surface within the article so that the absorbent capacity of the core can be more efficiently used. Such a distribution layer may be smaller in surface than the absorbent core's footprint and does typically not extend beyond the edges of the core's footprint. The distribution layer is typically made of a fibrous material, which may be based on synthetic or cellulosic fibers. The distribution layer may also comprise channels that may at least partially or completely match the positions and the shape of all or any of the channels of the absorbent core. The same consideration regarding the shape, position and orientation for the channels of the absorbent core can be re-applied for channels a distribution layer and thus will not be repeated herein.

The distribution layer may thus be a fibrous layer which has an average basis weight of at least 50 g/m$^2$, in particular from 50 g/m$^2$ to 300 g/m$^2$, and advantageously at least at least 100 g/m$^2$. The average basis weight is calculated by dividing the weight amount of the fibers by the area of the distribution where the fibers are present (including channel area in the distribution layer). The distribution layer may have a relatively low density. The density of the layer may vary depending on the compression of the article, but may typically range from 0.03 g/cm$^3$ to 0.25 g/cm$^3$, in particular from 0.05 g/cm$^3$ to 0.15 g/cm$^3$, measured at 0.30 psi (2.07 kPa). The density of the intermediate layer is measured at the centerpoint C of the article for this purpose.

The fibrous material may be manufactured by air-laying the fibers on a drum comprising several molds each having the required depth profile for the desired fibrous material configuration. The formed distribution layer can then be directly un-molded onto another component of the article such as a nonwoven carrier layer and then integrated with the rest of the article. There may be other layers between the distribution layer and any of the topsheet and the absorbent core, for example an acquisition layer 52. When a nonwoven acquisition layer is present in the article, the distribution layer may be for example deposited on this acquisition layer, the two layers being further joined to absorbent core and the rest of the article, as is known in the art.

The distribution layer is typically a fibrous layer. The distribution layer may be a nonwoven material comprising fibers that are bonded to each other so that the layer has a strong integrity and may be manipulated independently of a substrate. Alternatively, the distribution layer may be another type of fibrous layer, in particular the distribution layer may comprise or consist of loose fibers with no or weak intra-fiber bonds, the fibers being deposited on a supporting substrate at varying basis weight to form a profiled distribution. A typical example of distribution/intermediate material comprises or consists of cross-linked cellulose fibers. The distribution/intermediate layer may for example comprise at least 50% by weight of cross-linked cellulose fibers. The cross-linked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf). The cross-linked cellulosic fibers provide higher resilience and therefore higher resistance against the compression in the product packaging or in use conditions, e.g. under baby weight.

Exemplary chemically cross-linked cellulosic fibers suitable for a distribution layer are disclosed in U.S. Pat. Nos. 5,549,791, 5,137,537, WO95/34329 or US2007/118087. The distribution layer comprising cross-linked cellulose fibers may comprise other fibers, but this layer may comprise at least 50%, or 60%, or 70%, or 80%, or 90% or even up to 100%, by weight of the layer, of cross-linked cellulose fibers (including the cross-linking agents). While the distribution material may be comprised of cellulose fibers, in particular cross-linked cellulose fibers, other materials are possible.

Other Components

The absorbent articles of the invention can further comprise any other typical components known for the intended purpose of the article that are not illustrated in the Figures, such as a transverse barrier element extending across the topsheet to form a receptacle for bowel movement, a lotion application on the topsheet, a wetness indicator comprising a pH indicator disposed between the absorbent core and the backsheet, etc. These components are well-known in the art and will not be further discussed herein. Reference is made to WO2014/093310 where several examples of these components are disclosed in more details.

The absorbent article may also comprise at least one elastic waist band (also called elastic waist feature) disposed parallel to and along the back edge of the article and less commonly parallel to and along the front edge of the article. Such waistbands help providing improved fit and containment at the back and/or front edge of the article. The elastic waist feature is generally intended to elastically expand and contract to dynamically fit the wearer's waist. The elastic waist band may be constructed in a number of different configurations. Non-limiting examples of back and front waistbands can be found in WO2012/177400 and WO2012/177401 (Lawson), and U.S. Pat. Nos. 4,515,595, 4,710,189, 5,221,274 and 6,336,922 (VanGompel et al.).

Packages

A plurality of articles according to the invention may be packaged in a package for transport and sale. At least 50% of the articles, and preferably all the articles, in the package may be according to the invention. The articles may be folded and packaged as is known in the art. The package may be for example a plastic bag or a cardboard box. Diapers may typically bi-folded along the transversal axis and the ears folded inwardly before being packaged. The absorbent articles may be packed under compression so as to reduce the size of the packages, while still providing an adequate amount of absorbent articles per package. By packaging the absorbent articles under compression, caregivers can easily handle and store the packages, while also providing distribution and inventory savings to manufacturers owing to the size of the packages.

The absorbent articles may thus be packaged compressed at an In-Bag Compression Rate of at least 10%, in particular of from 10% to 50%, in particular from 20% to 40%. The "In-Bag Compression Rate" as used herein is one minus the height of a stack of 10 folded articles measured while under compression within a bag ("In-Bag Stack Height") divided by the height of a stack of 10 folded articles of the same type before compression, multiplied by 100; i.e. (1-In-Bag Stack Height/stack height before compression)*100, reported as a percentage. Of course, the stack in the bag does not need to have exactly 10 articles, rather the value measured for the height of stack of article in the package is divided by the number of articles in the stack and then multiplied by 10. The method used to measure the In-Bag Stack Height is described in further details in the Test Procedures. The articles before compression are sampled from the production line between the folding unit and the stack packing unit. The stack height before compression is measured by taking 10 articles before compression and packing, and measuring their stack height as indicated for the IBSH.

Packages of the absorbent articles of the present disclosure may in particular have an In-Bag Stack Height of less than 110 mm, less than 105 mm, less than 100 mm, less than 95 mm, less than 90 mm, specifically reciting all 0.1 mm increments within the specified ranges and all ranges formed therein or thereby, according to the In-Bag Stack Height Test described herein. For each of the values indicated in the previous sentence, it may be desirable to have an In-Bag Stack Height of greater than 60, or greater than 70 mm, or greater than 75 mm, or greater than 80 mm. Alternatively, packages of the absorbent articles of the present disclosure may have an In-Bag Stack Height of from 60 mm to 110 mm, from 75 mm to 110 mm, from 80 mm to 110 mm, from 80 mm to 105 mm, or from 80 mm to 100 mm, specifically reciting all 0.1 mm increments within the specified ranges and all ranges formed therein or thereby, according to the In-Back Stack Height Test described herein.

Relations Between the Layers and Components

Typically, adjacent layers will be joined together using conventional bonding method such as adhesive coating via slot coating or spraying on the whole or part of the surface of the layer, or thermo-bonding, or pressure bonding or combinations thereof. Most of the bonding between components is for clarity and readability not represented in the Figure. Bonding between the layers of the article should be considered to be present unless specifically excluded. Adhesives may be typically used to improve the adhesion of the different layers, for example between the backsheet and the core wrap. The adhesives used may be any standard hotmelt glue as known in the art. The individual components may be converted into an absorbent article according to any of the processes known in the art.

Process for Making

The topsheet 24, the backsheet 25, the absorbent core 28, the acquisition layer 52 and the other article components may be assembled in a variety of well-known configurations, in particular by gluing, heat-, ultrasonic- and/or pressure-bonding as is known in the art. These bonds are typically not represented in the Figures to preserve readability of the Figures, but are present as is known in the art. The topsheet can be attached directly or indirectly to an underlying layer such as the absorbent core through channels in an intermediate layer such as channels in a distribution layer. If the channels in the intermediate layer are material free, the topsheet may thus be bonded to the top side of the absorbent core through the channels of the acquisition or distribution layer for example by adhesive bonding (gluing). Indirect bonding of the topsheet to an underlying layer may be for example provided when an acquisition layer not comprising channels is present between the topsheet and a distribution layer with channels.

A process for making an absorbent core according to the invention may comprise the following steps of:
  providing a core wrap material;
  depositing an absorbent material on the core wrap material on a deposition area, wherein the deposition area comprises at least two channels substantially free of absorbent material;
  forming a core wrap having a top side and bottom side enclosing the absorbent material; so that the deposition area is between the top side and the bottom side of the core wrap;
  bonding both sides of the core wrap to another in at least a first channel to make a channel of the first type, while not bonding or weakly bonding the bottom side and the top side of the core wrap in a second channel to make a channel of the second type.

The process may advantageously comprise the step of applying an inner core glue on the inner surface of the core wrap material before and/or after the step of deposition the absorbent material so that at least a portion of the absorbent material area is adhesively immobilized on the top side and/or the bottom side of the core wrap.

The core wrap material can be as indicated before any usual material known in the art, typically a nonwoven. The absorbent material may be deposited as a layer on the core wrap material using any known suitable techniques. The deposition may be continuous, for example as in an airlaying process where a constant flow of particles and cellulose fibers are mixed in a chamber before being pulled by negative pressure towards the core wrap material on the other side of the airlaying chamber. The core wrap material may typically lay on a rotating drum while the absorbent material is deposited with the airlaying chamber being stationary. The outer surface of the drum comprises raised portions matching the shapes of the desired channels so that that substantially no absorbent material is deposited in these areas.

The core wrap may be formed according to any typical process used in absorbent core making. The core wrap material may be provided having a width more than twice as wide as the deposition area so that a span of the core wrap material can be folded over the absorbent material deposited on the rest of the core wrap, with a longitudinal bond (typically adhesive) between the overlapping spans of core wrap material to ensure core integrity. Alternatively the core wrap material may comprise a first substrate on which the absorbent material is deposited and forms a first side of the core wrap, with a second substrate being applied on top of the absorbent material, with both substrates being then typically bonded longitudinally along an overall (C-wrap or sandwich seals).

As discussed previously, an inner core glue may be typically on at least one, or both, of the inner surface of the top side and/or the bottom side of the core wrap to provide for better immobilization of the absorbent material. The inner core glue may also form or at least contribute to the bonds of the first type of channels (and optionally the second type as well, as long as the second type of bonds are weaker). The inner core glue may be applied as a pattern of longitudinally-extending stripes, or spirals, or any other pattern as is known in the art. The inner core glue may be applied on the core wrap material before the absorbent material is deposited thereon, or alternatively on the second part of the core wrap that is folded over, or separately added to the core wrap material.

The top side and the bottom side of the core wrap are bonded to make one or more channels of the first type, as indicated above. The bond in the first type of channels may be in particular provided by an inner core glue and an additional bonding means, in particular wherein the additional bonding means is a reinforcing glue and/or ultrasonic bonding and/or thermo bonding and/or additional pressure. The second type of channels may be completely unbonded, or if they comprise a weaker bond this bond may be in particular limited to a bond provided for example by the same inner core glue as the first type of bonds, but do not comprise an additional bonding means as indicated above. For example, the first type of bonds may be adhesive bonds wherein the top side and the bottom side of the core wrap have been locally pressed together to increase the strength of the adhesive bonds, while the core wrap in the second type of channels have not been pressed together, and thus do not form a strong bond even if they comprise some of the inner core glue. In another example, the first bond may be an adhesive bond complemented with an additional bonding means such as a thermo- or ultrasonic bond, and the second type of channels may comprise no bond or only the same type of adhesive bond as the first type of channels without the additional bonding means.

Test Procedures

The values indicated herein are measured according to the methods indicated herein below, unless specified otherwise. All measurements are performed at 21° C.±2° C. and 50%±5% RH, and samples should be kept at least 24 hours in these conditions to equilibrate before conducting the tests, unless indicated otherwise. For example the Static Peel Force Time is measured at 23 degrees as is indicated below.

Static Peel Force Time

The purpose of the Static Peel Force Time (SPFT) test method is to measure the bond strength between the top side and the bottom side of the core wrap within the channels. This test method measures how long the bond is able to withstand a constantly applied vertical force of about 150 grams (Static Peel Force Time) under standardized conditions.

Equipment

Figure 8:
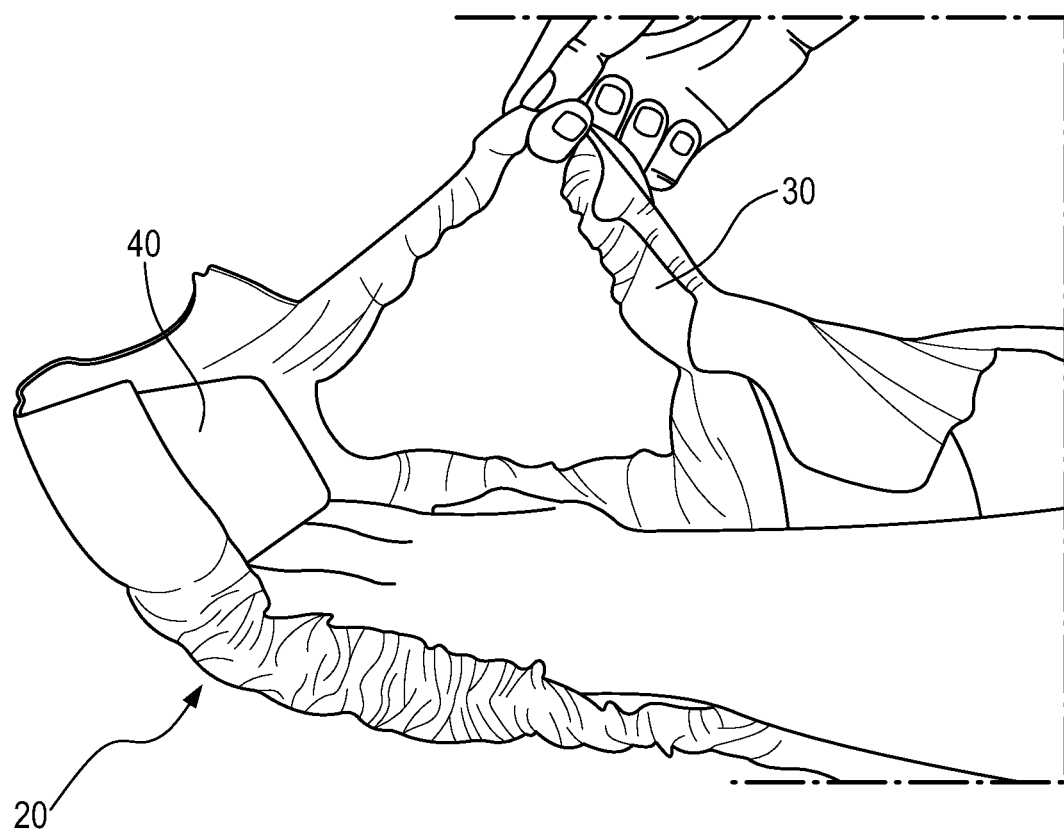
FIG. 8 illustrates the step of extracting the core from a finished article for measuring the Static Peel Force Time (SPFT) of the channels.

Core Preparation:

Typically the absorbent core is taken from a commercial article (e.g. diaper), and can be extracted from the article as follows (see FIG. 8):

1. Open the diaper topsheet side up and place it flat onto a table. For pants, open the side seams and remove waistbands. Hold the diaper with one hand and carefully remove the ears (40) and the barrier cuffs (30) along the cuffs continuous bond (outer edge) on both sides of the articles.
2. Gently remove topsheet and acquisition system without damaging the core end seals if present. The backsheet does not need to be removed.

Figure 9:
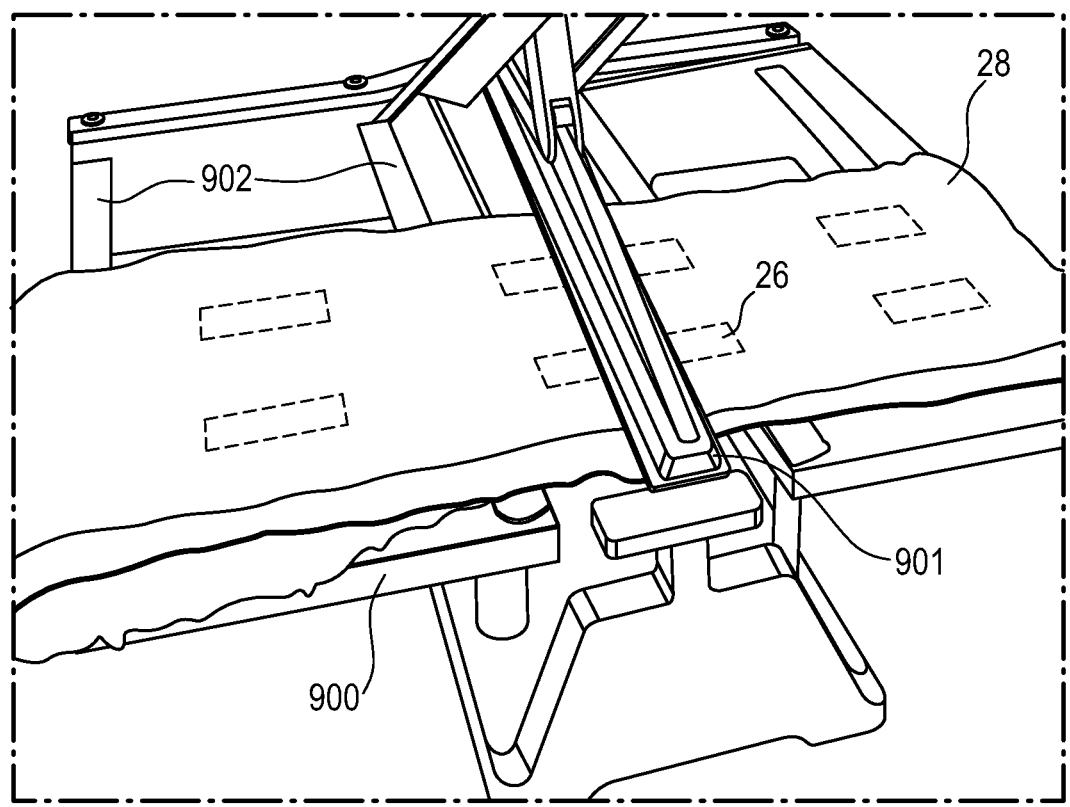
FIG. 9 illustrates the step of identifying and cutting a sample band of the core comprising a channel.
Figure 10:
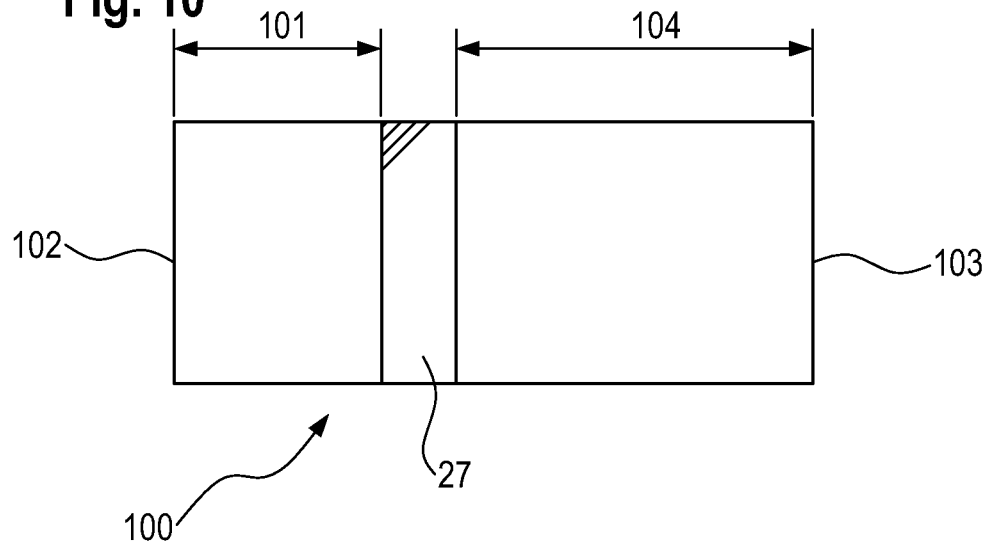
FIG. 10 illustrates the sample after being cut to be 1-inch wide.

Channel Sample Preparation (see FIG. 9):

1. Put each core under a lamp table or a UV-light to identify the beginning and the end of each channel.
2. Define the longitudinal center of the channel area by using a ruler and mark a line perpendicular to the longitudinal axis passing through the center of the channel area.
3. Lay the core (28) on a supporting table (900) fitted with the 25.4 mm wide cutter (901) and align to the centerline of the channel. Double sided tapes (902) may be used to keep the sample in place. The table comprises two grooves or gaps on each side of the area to be cut so that the cutter blade can penetrate through the thickness of the core.
4. Cut the core in transversal direction to obtain a sample band centered on the centerline of the channel, optionally check the width of the cut sample band (target=25±2 mm).
5. Use the scissors to cut the 1-inch wide sample band in the longitudinal direction to obtain a sample (100) comprising the channel bond (27). There should be at least a 5 mm channel-free flap (101) between the channel bond and the inner edge (102) of the sample to ensure proper manipulation of the sample—see FIG. 10. Obtain a left sample and right sample if applicable. Label the cut samples appropriately, e.g. left/right channels.
6. The sample will be clamped on the outer edge (103) during the test. The outer edge (103) of the sample can be trimmed with the scissors, however in order to carry the test, the minimum channel distance (104) to the

| | |
|---|---|
| Medium Clip | Medium Binder Clips 25 mm Capacity (#72050). ACCO World Product. Other suppliers: Yihai Products (#Y10003), Universal Office Products (#10210), Diamond (#977114), or equivalent. The clip weights 4.5 g +/− 1 g. |
| Large Clip | Large Binder Clips 2 inch (50.8 mm). ACCO World Product. Other suppliers: Yihai Products, Universal Office Products, Diamond, or equivalent |
| Test Stand | RT-10 room temperature (Shear Tester) w/ timer. ChemInstruments, 510 Commercial Drive, Fairfield Ohio 45014-9797, USA; or equivalent. Must be placed in a vibration free area. |
| Weight | 150 g (+/−1 g) TW150 Shear Tester Weight with hook on top (to attach to the clip). ChemInstruments, 510 Commercial Drive, Fairfield Ohio 45014-9797, USA; or equivalent |
| Cutting Tools | Scissors and a 25.4 mm (1 inch) cutter (convenient source, e.g. JDC Precision Sample Cutter made by Thwings-Albert Instrument Company Philadelphia USA, cat# 99, cut width 25.4 mm, accuracy at least +/−0.1 mm) |
| Metal Ruler | Traceable to NIST, DIN, JIS or other comparable National Standard, graduated in mm, longer than the length to be measured |
| Temperature | Testo-temperature device (or equivalent) to measure temperature at sample height with an accuracy of ±0.5° C. and ±2.5% RH in the range between −10° C. and +50° C. Testo GmbH & Co., Postbox 1140, D-79849 Lenzkirch (www.testo.com) Article number for Testo 625: 0563 6251. | outer edge (103) for the sample should be sufficient to ensure a proper clamping of the core wrap material into the clamps. Typically a minimum distance (104) between the channel and the outer edge should be of at least 5 mm for this purpose, 20 mm being ideal.

Figure 11:
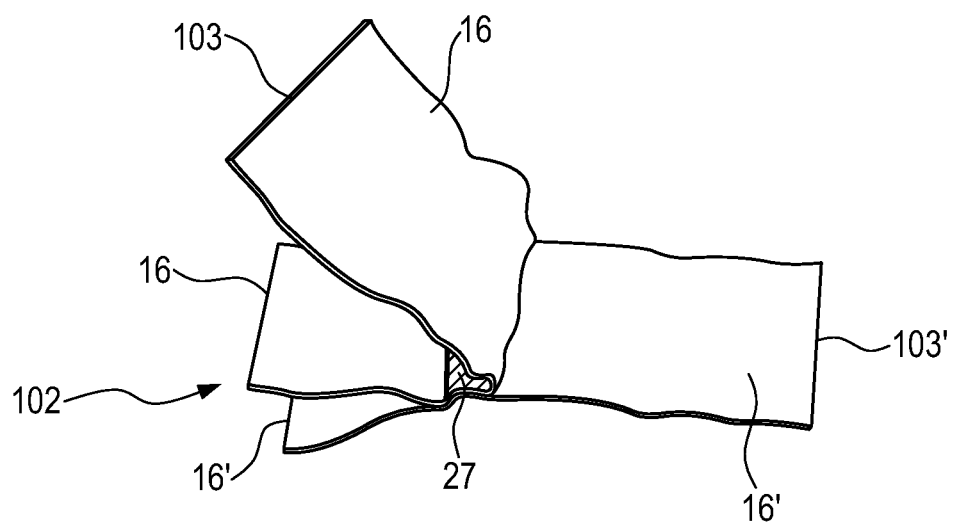
FIG. 11 shows the cut sample before placing it in the tester.

7. Gently remove any core absorbent material outside the channel that is between bottom side and the top side of the core wrap (see FIG. 11), for this open any core wrap longitudinal side deals on the outer edge (103) if needed in case the seals was trimmed away already.

Test Procedure (see FIG. 12):

Set up the tester in an area where the temperature is constant at 23° C. and ensure that the tester and the samples have at least 2 h time to reach this temperature.

1. Clamp the outer edge (103') of the bottom side (16') of the sample into the jaw of the large binder (120) clip hanging at the top of the tester bar.
2. Clamp the other binder clip (medium size) (121) to the top side (16) of the core wrap at its outer edge (103). The inner edge (102) of the sample is facing away from the experimenter.
3. Slowly attach the 150 g weight (122) to the medium binder clip and lower slowly until the weights hangs freely on the test sample.
4. As soon as the weight is released, push the timer reset button for that sample to begin the timer at 0 minutes. NOTE: The timer must be checked to ensure that it has begun counting from 0.0 min. The operator should look for the number to change from 0.0 min to 0.1 min.
5. Repeat procedure above for each sample prepared. The Test Stand allows testing several samples in parallel.
6. The timers will stop once the sample weight has fallen on the bottom plate due to the bond breaking. The bottom plate comprises a switch linked to the timer so that it automatically stops when the weight has fallen down. The time recorded is the Static Peel Force Time for that sample (expressed in minutes). Note: if the weight falls down due to the sample slipping out of the clip (121) without the bond breaking, the test needs to be rerun on a new sample.
7. If the sample weight has not fallen after 999 minutes, the Static Peel Force Time is reported to be 999 minutes (maximum Static Peel Force Time Time).
8. For a commercial article of a given construction, the experiment is repeated on 10 different samples extracted from 10 individual articles or cores, for example 10 randomly selected diapers in a commercially-sourced diaper package, and the result averaged. The Static Peel Force Time is this average.

Centrifuge Retention Capacity (CRC)

The CRC measures the liquid absorbed by the superabsorbent polymer particles for free swelling in excess liquid. The CRC is measured according to EDANA method WSP 241.2.R3 (12).

In-Bag Stack Height Test

The In-Bag Stack Height of a package of absorbent articles is determined as follows:

Equipment: A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams. Such a testing apparatus is for example illustrated on FIG. 19 of US 2008/0312624A1.

Test Procedure: Absorbent article packages are equilibrated at 21±2° C. and 50±5% relative humidity prior to measurement. The horizontal sliding plate is raised and an absorbent article package is placed centrally under the horizontal sliding plate in such a way that the absorbent articles within the package are in a horizontal orientation. Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

Miscellaneous

Unless indicated otherwise, the description and claims refer to the absorbent core and article before use (i.e. dry, and not loaded with a fluid) and conditioned at least 24 hours at 21° C.+/−2° C. and 50+/−5% Relative Humidity (RH).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a front side, a back side, a longitudinal axis notionally extending in a longitudinal direction from a middle of the front side to a middle of the back side, wherein the absorbent article has a first length measured along the longitudinal axis, the absorbent article notionally having a front region having a second length of one third of the first length of the absorbent article, a back region having a third length of one third of the first length of the absorbent article, and a crotch region between the front region and the back region having a fourth length of one third of the first length of the absorbent article;

the absorbent article comprising a topsheet on a wearer-facing side, a backsheet on a garment-facing side, and an absorbent core between the topsheet and the backsheet, wherein the topsheet is liquid permeable and the backsheet is liquid impermeable;

wherein the absorbent core comprises:
a core wrap comprising a top side and a bottom side;
an absorbent material between the top side and the bottom side of the core wrap and having a deposition area, wherein the absorbent material comprises cellulose fibers and superabsorbent polymer particles; and
at least two channels substantially free of absorbent material within the deposition area; wherein the at least two channels comprise at least one of a first type of channels and at least one of a second type of channels, wherein the top side and the bottom side of the core wrap are bonded to each other by a first bonding and an additional bonding in the first type of channels, and the top side and the bottom side of the core wrap are bonded by the first bonding but are not bonded by the additional bonding in the second type of channels, where in the first bonding is a different type of bonding than the additional bonding, and wherein the at least one of the first type of channels is separated in the longitudinal direction from the at least one of the second type of channels by at least 5 mm.

2. The absorbent article according to claim 1, wherein the first bonding comprises one of a group consisting of adhesive bonding, thermo bonding, mechanical bonding, ultrasonic bonding, and any combinations thereof.

3. The absorbent article according to claim 1, wherein the first type of channels have a first Static Peel Force Time and the second type of channels have a second Static Peel Force Time, wherein the first Static Peel Force Time is higher than the second Static Peel Force Time.

4. The absorbent article according to claim 1, wherein the absorbent core comprises two channels of the first type disposed as a symmetrical pair relative to the longitudinal axis.

5. The absorbent article according to claim 1, wherein the at least one of the first type of channels is at least partially present in the crotch region of the absorbent article.

6. The absorbent article according to claim 1, wherein the absorbent core comprises two channels of the second type disposed as a symmetrical pair relative to the longitudinal axis.

7. The absorbent article according to claim 1, wherein the at least one of the second type of channels is at least partially present in the front region of the absorbent article or is at least partially present in the back region of the absorbent article.

8. The absorbent article according to claim 1, wherein one or more channels of the first type and one or more channels of the second type do not extend to any of edges of the deposition area.

9. The absorbent article according to claim 1, wherein the first bonding comprises an inner core glue.

10. The absorbent article according to claim 9, wherein the inner core glue is present in at least one of:

between the absorbent material and the inner surface of the bottom side of the core wrap, and
between the absorbent material and the inner surface of the top side of the core wrap,
and the inner core glue at least partially overlaps with the deposition area of the absorbent material to at least partially immobilize the absorbent material.

11. The absorbent article according to claim 1, wherein a cumulated length of the at least one of the first type of channels and the at least one of the second type of channels projected on the longitudinal axis represent from 10% to 80% of the first length of the absorbent article.

12. The absorbent article according to claim 1, wherein the absorbent article further comprises an acquisition layer between the topsheet and the absorbent core.

13. The absorbent article according to claim 12, wherein the acquisition layer is a nonwoven acquisition layer.

14. The absorbent article according to claim 1, wherein the at least one of the first type of channels are separated from at least one of the second type of channels by a separating zone comprising the absorbent material.

15. The absorbent article according to claim 1, wherein the cellulose fibers and superabsorbent polymer particles are mixed.

16. The absorbent article according to claim 1, wherein the absorbent material comprises from 40% to 70% by weight of SAP particles.

17. A package comprising a plurality of the absorbent article of claim 1, wherein the package has an In-Bag Stack Height of less than 110 mm.

18. An absorbent core comprising:
a core wrap comprising a top side and a bottom side;
an absorbent material comprising cellulose fibers and superabsorbent polymer particles between the top side and the bottom side of the core wrap and having a deposition area; and
at least two channels substantially free of absorbent material within the deposition area; wherein the at least two channels comprise at least one of a first type of channels and at least one of a second type of channels, wherein the top side and the bottom side of the core wrap are bonded to each other by a first bonding and an additional bonding in the first type of channels, and the top side and the bottom side of the core wrap are not bonded by the additional bonding in the second type of channels, where in the first bonding is a different type of bonding than the additional bonding, and wherein the at least one of the first type of channels is separated in the longitudinal direction from the at least one of the second type of channels by at least 5 mm, and wherein the longitudinal direction extends along a longest dimension of the absorbent core.

19. A method for making an absorbent core, comprising the steps of:
providing a core wrap material;
applying an inner core glue on the core wrap material;
depositing an absorbent material comprising cellulose fibers and superabsorbent polymer particles on the core wrap material on a deposition area between the top side and the bottom side of the core wrap material, wherein the deposition area comprises at least two channels substantially free of absorbent material, and if inner core glue is present the deposition area at least partially corresponds to the inner core glue;
forming a core wrap having the top side of the core wrap material and the bottom side of the core wrap material enclosing the absorbent material; and forming a first type of channels of the at least two channels and a second type of channels of the at least two channels by forming the first type of channels using a first bonding and an additional bonding to bond the top side and the bottom side of the core wrap to each other in the first type of channels, and forming the second type of channels with the first bonding and without the additional bonding between the top side and the bottom side of the core wrap in the second type of channels, where in the first bonding is a different type of bonding than the additional bonding, and wherein the first type of channels is separated in the longitudinal direction from the second type of channels by at least 5 mm, and wherein the longitudinal direction extends along a longest dimension of the absorbent core.

20. The method of claim 19 wherein the first bonding comprises the inner core glue.

\* \* \* \* \*